(12) United States Patent
Osman et al.

(10) Patent No.: US 8,091,801 B2
(45) Date of Patent: *Jan. 10, 2012

(54) GENERATION OF THERAPEUTIC MICROFOAM

(75) Inventors: Tariq Osman, London (GB); Sheila Bronwen Shilton-Brown, Brentwood (GB); David Dakin Iorwerth Wright, High Wycombe (GB); Anthony David Harman, Henley-on-Thames (GB); Timothy David Boorman, Frinton on Sea (GB)

(73) Assignee: BTG International Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/487,387

(22) Filed: Jun. 18, 2009

(65) Prior Publication Data

US 2009/0256006 A1 Oct. 15, 2009

Related U.S. Application Data

(60) Continuation of application No. 12/039,341, filed on Feb. 28, 2008, now abandoned, which is a division of application No. 11/171,293, filed on Jul. 1, 2005, now Pat. No. 7,357,336, which is a continuation of application No. 09/979,655, filed as application No. PCT/GB00/02045 on May 26, 2000, now Pat. No. 6,942,165.

(30) Foreign Application Priority Data

May 26, 1999 (GB) .................................. 9912356.4

(51) Int. Cl.
*F23D 11/24* (2006.01)
*A61F 2/00* (2006.01)

(52) U.S. Cl. .......................... 239/337; 424/423; 514/945
(58) Field of Classification Search .................. 239/337; 424/400, 423, 600, 43, 44, 45, 46, 47, 9.5, 424/9.51, 450, 76.2, 484; 514/945, 724, 514/738, 706, 708; 604/140
See application file for complete search history.

(56) References Cited

U.S. PATENT DOCUMENTS 2,630,183 A 3/1953 Foutz
(Continued)

FOREIGN PATENT DOCUMENTS

CA 1 232 837 2/1988
(Continued)

OTHER PUBLICATIONS

Cabrera, Juan, "Echo-Sclerotherapy of Long Saphenous Veins and Venous Malformations With Sclerosing Agents in Microfoam Long-Term Outcomes," A Joint meeting of the Canadian Society of Phlebology and The Sclerotherapy Society of Australia, The Transpacific Phlebology Forum, 112, Jun. 27-Jul. 1, 1997, Australia.

(Continued)

*Primary Examiner* — Len Tran
*Assistant Examiner* — Steven M Cernoch
(74) *Attorney, Agent, or Firm* — Finnegan, Henderson, Farabow, Garrett & Dunner, L.L.P.

(57) ABSTRACT

Improved therapeutic sclerosing microfoams and methods and devices for making them are provided that have advantage in producing a consistent profile injectable foam with minimal input by the physician yet using high volume percentages of blood dispersible gases, thus avoiding use of potentially hazardous amounts of nitrogen.

12 Claims, 9 Drawing Sheets

U.S. PATENT DOCUMENTS

Figure 1:
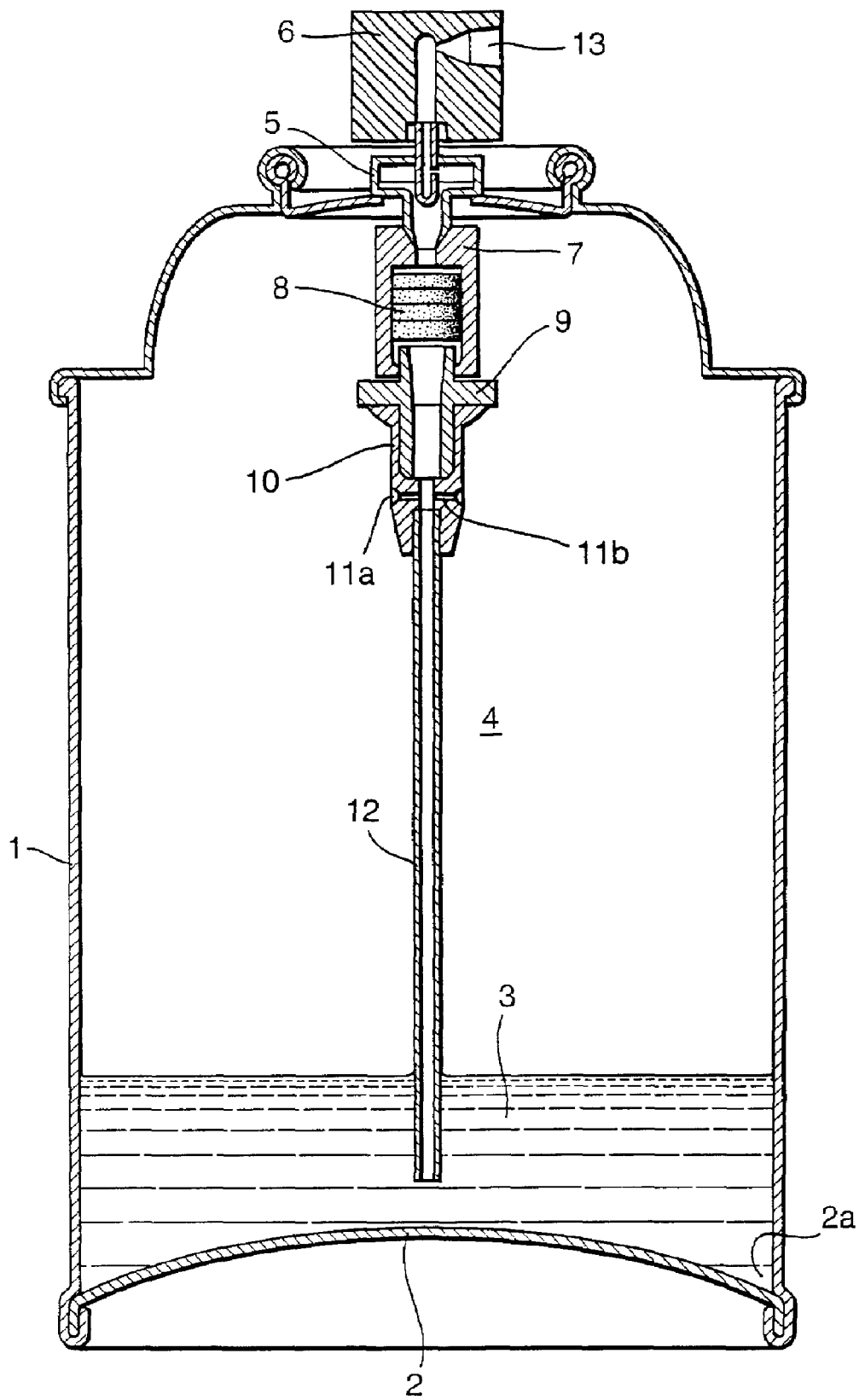

| Number | Kind | Date | Inventor |
|---|---|---|---|
| 2,724,383 | A | 11/1955 | Lockhart |
| 3,698,453 | A | 10/1972 | Morane et al. |
| 3,767,085 | A | 10/1973 | Cannon et al. |
| 3,955,720 | A | 5/1976 | Malone et al. |
| 3,970,219 | A | 7/1976 | Spitzer et al. |
| 4,019,657 | A | 4/1977 | Spitzer et al. |
| 4,040,420 | A | 8/1977 | Speer |
| 4,127,131 | A | 11/1978 | Vaillancourt |
| 4,276,885 | A | 7/1981 | Tickner et al. |
| 4,292,972 | A | 10/1981 | Pawelchak et al. |
| 4,328,107 | A | 5/1982 | Wright |
| 4,466,442 | A | 8/1984 | Hilmann et al. |
| 4,538,920 | A | 9/1985 | Drake |
| 4,718,433 | A | 1/1988 | Feinstein |
| 5,048,750 | A | 9/1991 | Tobler et al. |
| 5,064,103 | A | 11/1991 | Bennett |
| 5,071,379 | A | 12/1991 | Poizot |
| 5,084,011 | A | 1/1992 | Grady |
| 5,141,738 | A | 8/1992 | Rasor et al. |
| 5,368,231 | A | 11/1994 | Brunerie et al. |
| 5,425,366 | A | 6/1995 | Reinhardt et al. |
| 5,425,580 | A | 6/1995 | Beller |
| 5,454,805 | A | 10/1995 | Brony |
| 5,542,935 | A | 8/1996 | Unger et al. |
| 5,556,610 | A | 9/1996 | Yan et al. |
| 5,623,085 | A | 4/1997 | Gebhard et al. |
| 5,656,200 | A | 8/1997 | Boettcher et al. |
| 5,676,962 | A * | 10/1997 | Cabrera Garrido et al. .. 424/423 |
| 5,733,572 | A | 3/1998 | Unger et al. |
| 5,902,225 | A | 5/1999 | Monson |
| 6,053,364 | A | 4/2000 | van der Heijden |
| 6,536,629 | B2 | 3/2003 | van der Heijden |
| 6,561,237 | B1 | 5/2003 | Brass et al. |
| 6,572,873 | B1 * | 6/2003 | Osman et al. ................. 424/423 |
| 6,605,066 | B1 | 8/2003 | Gravagna et al. |
| 6,942,165 | B1 * | 9/2005 | Osman et al. ................. 239/337 |
| RE38,919 | E | 12/2005 | Garrido et al. |
| 7,025,290 | B2 * | 4/2006 | Osman et al. ................. 239/337 |
| 7,357,336 | B2 * | 4/2008 | Osman et al. ................. 239/337 |
| 7,604,185 | B2 | 10/2009 | Osman et al. |
| 2002/0031476 | A1 | 3/2002 | Trevino et al. |
| 2002/0056730 | A1 | 5/2002 | van de Heijden |
| 2002/0077589 | A1 | 6/2002 | Tessari |
| 2002/0101785 | A1 | 8/2002 | Edwards et al. |
| 2004/0156915 | A1 | 8/2004 | Harman et al. |
| 2005/0002873 | A1 | 1/2005 | Harman et al. |
| 2006/0049269 | A1 | 3/2006 | Osman et al. |
| 2006/0062736 | A1 | 3/2006 | Wright et al. |
| 2006/0280690 | A1 | 12/2006 | Wright et al. |
| 2007/0003488 | A1 | 1/2007 | Wright et al. |
| 2007/0003489 | A1 | 1/2007 | Wright et al. |
| 2007/0031345 | A1 | 2/2007 | Harman et al. |
| 2007/0031346 | A1 | 2/2007 | Harman et al. |
| 2007/0104651 | A1 | 5/2007 | Wright et al. |
| 2008/0145401 | A1 | 6/2008 | Osman et al. |
| 2008/0274060 | A1 | 11/2008 | Wright et al. |

FOREIGN PATENT DOCUMENTS

| Country | Number | Date |
|---|---|---|
| DE | 26 08 771 A1 | 9/1976 |
| DE | 3048744 A1 | 7/1982 |
| DE | 3050812 C2 | 3/1985 |
| DE | 8704600.8 | 11/1987 |
| DE | 3417182 C2 | 1/1989 |
| EP | 0586875 | 3/1974 |
| EP | 00 11 381 | 5/1980 |
| EP | 0 054 728 A1 | 6/1982 |
| EP | 0 077 752 | 4/1983 |
| EP | 0 123 235 | 10/1984 |
| EP | 0 131 540 | 1/1985 |
| EP | 0 217 582 A2 | 4/1987 |
| EP | 0 324 938 A1 | 7/1989 |
| EP | 0 359 246 | 3/1990 |
| EP | 0 564 505 | 10/1993 |
| EP | 06 13 836 A1 | 9/1994 |
| EP | 2 068 151 | 4/1995 |
| EP | 0 656 203 A1 | 6/1995 |
| EP | 1716871 | 1/1996 |
| EP | 0 997 396 A1 | 5/2000 |
| FR | 1 547 768 | 11/1969 |
| FR | 2 672 038 | 7/1992 |
| FR | 2 775 436 | 9/1999 |
| GB | 2369996 | 6/2002 |
| JP | 10081895 | 3/1998 |
| JP | H8-235664 | 3/1998 |
| JP | H10-81895 | 3/1998 |
| WO | WO 92/05806 | 4/1992 |
| WO | WO 92/11873 | 7/1992 |
| WO | WO 93/05819 | 4/1993 |
| WO | WO 94/21384 | 9/1994 |
| WO | WO 95/00120 | 1/1995 |
| WO | WO 96/08227 | 3/1996 |
| WO | WO 96/25194 | 8/1996 |
| WO | WO 96/38180 | 12/1996 |
| WO | WO 97/13585 | 4/1997 |
| WO | WO 99/43371 | 9/1999 |
| WO | WO 00/24649 | 5/2000 |
| WO | WO 00/66274 | 11/2000 |
| WO | WO 00/72821 A1 | 12/2000 |
| WO | WO 00/78629 | 12/2000 |
| WO | WO 02/058834 | 8/2002 |
| WO | WO 03/013475 | 2/2003 |
| WO | WO 2004/047969 | 6/2004 |
| WO | WO 2005/115484 A1 | 8/2005 |

OTHER PUBLICATIONS

Cabrera, J., "Treatment of Venous Malformations with Sclerosant in Microfoam Form," Arch Dermatol, vol. 139, 2003, 1409-1416.

Henriet, J.P. "One Year of Daily Application of Sclerotherapy (Reticular Veins and Telangiectases) Using Polidocanol Foam: Feasibility, Results, Complications," Phlebologie, 1997, 50, No. 3, 355-360, Britain.

Monfreux, A., "Sclerosant Treatment of Saphenous Truncs and Their Large Calibre Collaterals by the MUS Method," Phlebologie, 1997, 50, No. 3, 351-353.

Tessari, L., "New Technique for Obtaining Sclero-Foam," Phlebologie, 2000, 53, No. 1, 129.

Anon, "New Drugs," Australian Prescriber, vol. 25, pp. 20-23 (2002).

Cavezzi, A., "Duplex Guided Sclerotherapy of Long and Short Saphenous Vein With Sclerosing Foam," InFoam Sclerapy State of Art, ed. J.P. Heneriet, Editions Phlébologique Francais pp. 61-71 (2002).

Garcia Mingo J., "Foam Medical System," In Foam Sclerotherapy State of the Art, ed. J.P. Heneriet, Editions Phlébologique pp. 45-50 (2002).

Henriet, J.P., "History of Foam," In Foam Sclerotherapy State of the Art, ed. J.P. Heneriet, editions Phlébologique Francais pp. 13-15 (2002).

Robertson, C.S., "A Study of the Local Toxicity of Agents Used for Variceal Injection Sclerotherapy," HPB Surgery, 1989, vol. 1, pp. 149-154.

Sadoun, S., "Sclerosing Foam: Material and Methods," In Foam Sclerotherapy State of the Art, ed. J.P. Heneriet, editions Phlébologique Francais pp. 25-32 (2002).

Sica, M., "Ultrasound Appearance of Sclerosing Foam," In Foam Sclerotherapy State of the Art, ed. J.P. Heneriet, editions Phlébologique Francais pp. 85-88 (2002).

Tessari, L., "The Tourbillon Turbulence," In Foam Sclerotherapy State of the Art, ed. J.P. Heneriet, editions Phlébologique Francais pp. 51-55 (2002).

Office Action dated Nov. 14, 2008 for U.S. Appl. No. 10/536,862.

Material Safety Data Sheet for polydocanol (2009).

Chart of microfoam patents and applications.

Cho, Kyung J., "Carbon Dioxide Angiography," http://www.emedicine.com/radio/TOPIC870.HTM (2008).

Wollmann, J.C., "Sclerosant Foams" Phlebologie, 2010, 39: 208-17.

Office Action dated Nov. 14, 2008 for U.S. Appl. No. 10/536,862.

Co-pending U.S. Appl. No. 10/536,862, filed May 27, 2005.

Co-pending U.S. Appl. No. 10/522,529, filed Aug. 11, 2006.

Office Action dated May 6, 2009 for U.S. Appl. No. 10/522,529.

Co-pending U.S. Appl. No. 11/128,265, filed May 13, 2005.

Office Action dated Dec. 19, 2008, in co-pending U.S. Appl. No. 11/128,265.
Office Action dated Jun. 12, 2008, in co-pending U.S. Appl. No. 11/128,265.
Office Action dated Jan. 9, 2008, in co-pending U.S. Appl. No. 11/128,265.
Co-pending U.S. Appl. No. 10/522,525, filed Nov. 1, 2005.
Office Action dated Apr. 15, 2009, in co-pending U.S. Appl. No. 10/522,525.
Office Action dated Aug. 6, 2008, in co-pending U.S. Appl. No. 10/522,525.
Office Action dated Feb. 20, 2008, in co-pending U.S. Appl. No. 10/522,525.
Office Action dated Jul. 25, 2007 in co-pending U.S. Appl. No. 10/522,525.
Co-pending U.S. Appl. No. 10/522,528.
Office Action dated Jun. 5, 2009 in co-pending U.S. Appl. No. 10/522,528.
Office Action dated Oct. 16, 2008 in co-pending U.S. Appl. No. 10/522,528.
Co-pending U.S. Appl. No. 10/522,527, filed Oct. 10, 2006.
Office Action dated Apr. 28, 2009, in co-pending U.S. Appl. No. 10/522,527.
Office Action dated Aug. 6, 2008, in co-pending U.S. Appl. No. 10/522,527.
Office Action dated Nov. 1, 2007, in co-pending U.S. Appl. No. 10/522,527.
Co-pending U.S. Appl. No. 11/914,192.
Notice of Publication of Application dated May 14, 2009, in co-pending U.S. Appl. No. 11/914,192.
Co-pending U.S. Appl. No. 10/890,267.
Co-pending U.S. Appl. No. 11/914,190.
Co-pending U.S. Appl. No. 11/225,860.
Co-pending U.S. Appl. No. 11/171,293.
Co-pending U.S. Appl. No. 10/432,328.
Communication from the Examining Division of the European Patent Office in EP04798564, dated Apr. 26, 2007.
Reply to Communication from the Examining Division of the European Patent Office in EP04798564, dated Jan. 18, 2008.
Office Action dated Sep. 3, 2009, in co-pending U.S. Appl. No. 11/914,192.
German Nullity Action Complaint filed Jul. 27, 2001.
German Nullity Action First Brief filed Dec. 3, 2001.
German Nullity Action Supplemental Brief filed Dec. 31, 2002.
German Nullity Action Kreusler Brief filed Jan. 27, 2003.
German Nullity Action Decision by German Court.
German Nullity Action English Translation of the Substantiation of Appeal to the Federal Court of Justice on Sep. 26, 2003.
German Nullity Action English Translation of the Reply to appeal dated Feb. 12, 2004.
Meyer's Encyclopedia, 5$^{th}$ Edition, 1895, vol. 15, pp. 386.
R. Bayeux, "Comparative Resistance of Dog and Rabbit to Intravenous Injection of Oxygen", Compt. Rend. vol. 156, pp. 1329-1331, 1913.
F.W. Tunnicliffe et al., "The Intravenous Injection of Oxygen Gas as a Therapeutic Measure", Lancet, vol. II, pp. 321-323, 1916.
G. Galata, "Intravenous Injection of Oxygen in Dogs", Archivio di Fisiologia, vol. 21, pp. 331-350, 1923.
L. Moszkowiez, "Treatment of Varicose Veins with Sugar Injections, combined with vein ligation", Zentralblatt fur Chirurgie, No. 28, pp. 1731-1736, 1927.
G. de Takats, "Ambulatory Ligation of the Saphenous Vein", The Journal of the American Medical Association, vol. 94, No. 16, pp. 1194-1197, Apr. 19, 1930.
G. de Takats et al., "The Injection Treatment of Varicose Veins", Surgery, Gynecology and Obstetrics, vol. L, No. 3, pp. 545-561, Mar. 1930.
De L'Academie des Sciences, Conformement A Une Decision de L'Academie, pp. 890-892, Jan. 1930.
I.S. Tunick et al., "Sodium Morrhuate as a Sclerosing Agent in the Treatment of Varicose Veins", Annals of Surgery, vol. XCV, pp. 734-737, 1932.

H. Jausion, "Glycerine Chromee et Sclerose des Ectasies Veineuses", La Presse Medicale, No. 53, pp. 1061-1063, May 5, 1933.
G. de Takats et al., "Ligation of the Saphenous Vein", A report on Two Hundred Ambulatory Operations, Archives of Surgery, vol. 26, No. 1, pp. 72-88, Jan. 1933.
H. Harkins et al., "Embolism by Air and Oxygen: Comparative Studies", Proceedings of the Society for Experimental Biology and Medicine, vol. 32, pp. 178-181, 1934-35.
L. Ferguson, "Ligation of Varicose Veins, Ambulatory Treatment Preliminary to Sclerosing Injections", Annals of Surgery, vol. CII, pp. 304-314, 1935.
A. Ochsner et al., "Comparative Value of Intravenous Sclerosing Substances", Archives of Surgery, vol. 29, No. 3, pp. 397-416, Sep. 1934.
H. Biegeleisen, "Fatty Acid Solutions for the Injection Treatment of Varicose Veins", Annals of Surgery, vol. CV, pp. 610-615, 1937.
A. Schmier, "Clinical Comparison of Sclerosing Solutions in Injection Treatment of Varicose Veins, Delayed Slough: Recurrence of Varices", The American Journal of Surgery, vol. XXXVI, No. 1, pp. 389-397, Apr. 1937.
R.M. Moore et al., "Injections of Air and Carbon Dioxide into a Pulmonary Vein", Annals of Surgery, vol. 112, pp. 212-218, 1940.
W. Heyerdale et al., "Management of Varicose Veins of the Lower Extremities", Annals of Surgery, vol. 114, pp. 1042-1049, 1941.
R. Rowden-Foote; "Varicose Veins Hemorrhoids and Other Conditions—Their Treatment by Injection"; London, H.K. Lewis & Co. Ltd.; pp. 13-45, 106-119; 1944.
E.J. Orbach; "Sclerotherapy of Varicose Veins—Utilization of and Intravenous Air Block"; American Journal of Surgery; vol. LXVI, No. 3, pp. 362-366; Dec. 1944.
R.E. Weston et al., "The Influence of Denitrogenation on the Response of Anesthetized Dogs to Intravenously Injected Oxygen", vol. 26, pp. 837-848, 1946.
L. Reiner, "The Activity of Anionic Surface Active Compounds in Producing Vascular Obliteration", Surface Active Sclerosing Agents, Proceedings of the Society for Experimental Biology and Medicine, vol. 62, pp. 49-54, May-Jun. 1946.
R. Zingg, "Experimental tests with the new sclerosing agent "Geigy"", pp. 1-9, 1948.
R. Foote, "Treatment", Varicose Veins, Chapter 5, p. 65 and 86, 1949.
K. Sigg, "Newer Aspects of the Technique of Treating Varicosities", Therapeutishce Umschau, vol. 6, pp. 127-134, Dec. 1949.
K. Sigg, "The Ambulatory Treatment of Phlebitis", Schwiezerische Medizinische Wochenschrift, vol. 80, No. 2, Jan. 1950.
E.J. Orbach et al., The Thrombogenic Property of Foam of a Synthetic Anionic Detergent (Sodium Tetradecyl Sulfate N.N.R.), Thrombogenic Property of a Detergent, vol. 1, pp. 237-243, 1950.
R. Jung, "Injection Treatment of Varicose Veins", Praxis, pp. 195-198, 1950.
E.J. Orbach, "Contributions to the Therapy of the Varicose Complex", Journal of the International College of Surgeons, pp. 765-771, Jun. 1950.
H. Rogge, "On the dangers of sclerosing recurring varicose veins", Deutsche Medizinische Wochenschrift, No. 9, p. 301, 1950.
E.J. Orbach et al.; "The Thrombogenic Property of Foam of a Synthetic Anionic Detergent (Sodium Tetradecyl Sulfate N.N.R.)", Angiol 1, pp. 237-243; 1950.
Sigg, "Regarding treatment of varicose veins and their complications", Dermatologica, vol. 100, p. 317, 1950.
G. de Takats et al., "Division of the Popliteal Vein in Deep Venous Insufficiency of the Lower Extremities", Society for Vascular Surgery Issue, vol. 29., No. 3, pp. 342-354, Mar. 1951.
R.S. Handley, "The Treatment of Varicose Veins", The Practitioner—Diseases of the Veins, No. 993, vol. 166, pp. 228-235, Mar. 1951.
H.E. Lockhart-Mummery et al., "Varicose Ulcer—A Study of the Deep Veins with Special Reference to Retrograde Venography", The British Journal of Surgery, vol. XXXVIII, No. 151, pp. 284-295, Jan. 1951.
M. Mairano, "Metodo combinato chirurgico-sclerosante o metodo sclerosante semplice nel trattamento delle varici essenziali?" Minerva Chirurgica, vol. VI, No. 16, pp. 244-247, May 1951.

E. Orbach, "Leg Ulcers of Vascular Origin and Their Therapy" The American Journal of Surgery, vol. LXXXI, No. 5, pp. 568-572, May 1951.

M. Battezzati et al., "Treatment of Lower Limb Varices with Multiple Endermic Ligations and Sclerosant Injections Combined or not with Stripping of the long Saphenous Vein's higher region", Minerva Chirurgica, pp. 936-939, 1952.

H. Leonhardt, "On the Treatment of Extensive Formation of Varicose Veins with Ligature of the v. Saphena and Varicoid Injection Through Distally Inserted Ureteral Catheter", Ärztliche Wochenschrift, vol. 7, No. 3, pp. 56-58, Jan. 1952.

G. Mayer, "The Treatment of Varicose Veins from the point of View of Sclerotherapy, in particularly on the Basis of Varicophtine", Münchener Medizinische Wochenschrift, vol. 16, No. 20, Cols. 1037-1039, Jan. 1952.

H.G. Oden, "Can the Results of the Treatment of Varicose Vains and Ulcus Cruris be Improved?", Münchener Medizinische Wochenschrift, vol. 22, No. 8, pp. 364, Jan. 1952.

P. Piulaches et al., "Pathogenic Considerations on Varicose Veins Developed in Pregnancy", Lyon Chirurigical, Bulletin official de la Socirte de Chriurgie de Lyon, vol. 47, No. 3, pp. 263-278, Apr. 1952.

P. Jaeger, "The Current Treatment Standard for Crural Ulcer and Varices", Deutsche Medizinische Wochenschrift, vol. 77, No. 14, pp. 421-425, Apr. 4, 1952.

K. Sigg, "The Treatment of Varicosities and Accompanying Complications", Angiology, The Journal of Vascular Diseases, vol. 3, No. 5, pp. 355-379, Oct. 1952.

H. Wefers et al., "Results of Injection Treatment with Regard to Extreme Varication", Zentralblatt für Chirurgie, Issue No. 43, pp. 1825-1828, 1952.

K. Sigg, 'The Foamed Rubber Compression for Phlebitis and for Phlebitic and Varicose Complications38 , Die Medizinische, No. 27-28, pp. 910-915, Jul. 1952.

P. Piulachs et al., "Pathogenic Study of Varicose Veins", Angiology, The Journal of Vascular Diseases, vol. 4, No. 1, pp. 59-100, Feb. 1953.

F. Kunkel, "Medical Journal of Munich", $95^{th}$ year of edition, vol. 30, No. 44, p. 53, 1953.

Von Hans Brücke et al., "The combined foam sclerosis of varices", Wiener Medizinische Wochenschrift, vol. 104, No. 1, pp. 111-113, Jan. 1954.

G. de Takats et al., "Aneurysms: General Considerations", Angiology, The Journal of Vascular Disease, vol. 5, No. 3, pp. 173-208, Jun. 1954.

A. Hauser et al., "Prophylaxis of Phlebitis and Treatment of Varices During Pregnancy", Schweizerische Medizinische Wochenschrift, $84^{th}$ year, No. 1, pp. 13-14, Jan. 2, 1954.

G.D. Lilly et al., "An Evaluation of "High" Lumbar Sympathectomy in Arteriosclerotic Circulatory Insufficiency of the Lower Extremities", Surgery, Original Communications, vol. 35, No. 1, pp. 40-44, Jan. 1954.

Maarz, "Nil nocere!: Life-Threatening anaphylactic Incidents in Connection with Sclerosing of Varicose Veins", Munchener Medizinische Wochenschrift, vol. 27, No. 35, 1954.

E.J. Orbach, "Allergenic Tissue Reaction of Catgut, an Aid for the Obliteration of Varicose Veins", The Journal of the International College of Surgeons, vol. XXII, No. 6, pp. 707-710, Dec. 1954.

H. Leidinger, Sclerosation with air-block technique (Variocid plus Varicocid foam), Medizinische Klinik, pp. 1183-1184, 1954.

J and P Vacheron, "Essential Varicose Veins on Lower Limbs: Sclerosant Treatment by Streaming", Archives of Cardio-Vascular Diseases, $7^{th}$ Year, No. 12, pp. 1033-1038, Dec. 1954.

A. Ree, "Varicose Vein Treatment with Foam of Etamolin", Dansk Lmgeforening, No. 12-15, pp. 452-453, Jun. 1955.

A. Hübner, "Der Chirurg, Journal for All Fields of Surgical Medicine", $26^{th}$ Year of Edition, 1955.

H. Dodd, "The 'Stripping' Operation for Varicose Veins", The Postgraduate Medical Journal, vol. 31, pp. 73-78, 1955.

F. Jaeger, "Primary or Secondary Varicose Veins", Die Medizinische, No. 36, pp. 1237-1340, Sep. 1955.

W. Leun et al., "The Limits and Risks of the Sclerotherapy of Varicose Veins", German Medical Weekly Journal, No. 7, pp. 257-260, Feb. 18, 1955.

F. Schörcher, "For the Practice Varicose Veins and Deep Chronic Crural Thrombosis", Münchener Medizinische Wochenschrift, No. 41, pp. 1354-1358, Oct. 14, 1955.

K. Sigg, "The Treatment of Leg Ulcers", Die Medizinische, No. 17, pp. 646-648, 1955.

K. Sigg, "Therapeutic Issues—On the Treatment of Vein Thrombosis with Butazolidin", Schweizerische Medizinische Wochenschrift, $65^{th}$ year of the edition, No. 11, pp. 261-262, Mar. 12, 1955.

M.H. Steinberg, "Evaluation of Sotradecol in Sclerotherapy of Varicose Veins", Angiology The Journal of Vascular Diseases, vol. 6, No. 6, pp. 519-532, Dec. 1955.

P. Koistinen, "Eräitä näkökohtia alaraajojen laskimon-laajentumien hoidosta ja ennusteesta", Duodecim, vol. LXXII, No. 12, pp. 1000-1015, 1956.

Flückiger, P., Brugg, "Non-Surgical Retrograde Sclerosis of Varicose Veins With Varsyl Foam," Schweizerische Medizinische Wochenschrift No. 48, pp. 1368-1370, 1956.

R.W. Décoppet, "The Sclerotherapy of Varices with Thrombophilic Patients", Swiss Medical Weekly Journal, $86^{th}$ year, No. 20, pp. 509-513, May 19, 1956.

R. May, "Impairments and Risks of the Treatment of Varicose Veins", Münchener Medizinische Wochenschrift, No. 1, pp. 13-16, Jan. 1956.

E. Rappert, "The Therapy of Varicose Crural Ulcers", Wiender Medizinische Wochenschrift, vol. 106, No. 48, pp. 999-1000, Dec. 1, 1956.

K. Sigg, "Varicose Veins and Deep Seated Chronic Leg Vein Thrombosis" Münchener Medizinische Wochenschrift, vol. 98, No. 8, pp. 260-263, Feb. 1956.

M.J. Oppenheimer et al., "In vivo Visualization of Intracardiac Structures with Gaseous Carbon Dioxide—Cardiovascular-Respiratory Effects and Associated Changes in Blood Chemistry", American Journal of Physiology, vol. 186, pp. 325-334, Jul.-Sep. 1956.

K. Sigg, "Treatment of Superficial and Deep Thrombosis and the Application of Butazolidine", Gynaecologia, Supplementum ad vol. 144, pp. 19-23, Jul. 2 to 4, 1956.

K. Sigg, "A Good Prophylaxis of Thrombosis during Pregnancy, delivery and childbed as well as for Operations can Prevent the Thrombo-Embolism", Munchener Medizinische Wochenschrift, vol. 99, No. 17, p. 581 and 610-613 Apr. 1957.

H. Mayer et al., "Angiology: The Aetiology and Treatment of Varicosities of the Lower Extremity," Chirurgische Praxis, pp. 521-528, 1957.

T. Durant, et al., "The Safety of Intravascular Carbon Dioxide and its Use for Roentgenologic Visualization of Intracardiac Structures", Annals of Internal Medicine, vol. 47, No. 2, pp. 191-201, Aug. 1957.

R.R. Foote, "Varicose Vein Problems in General Practice", The Practitioner—Medical Etiquette, vol. 179, No. 179, pp. 59-66, Jul. 1957.

E.J. Orbach, "Reappraisal of the Sclerotherapy of Varicose Veins", Angiology—The Journal of Vascular Diseases, vol. 8, No. 6, pp. 520-527, Dec. 1957.

E. Rappert, "The treatment of varicose veins following a phlebitis and thrombosis", Winer Medizinische Wochenschrift, No. 4, pp. 100-101, 1957.

G. Savonuzzi et al., "A Therapeutic Method that Combines Sclerosing Agents and Anticoagulants for varicose diseases of the lower limb", Minerva Medical, vol. XLVIII, No. 24, pp. 1124-1126, Mar. 24, 1957.

Von H. Westhues et al., "The Varicose Symptom Complex", Medizinische Klinik, No. 16, pp. 657-660, 1957.

Willenegger et al., "Attempt at carrying out Thromboembolism Propylaxis without Anticoagulants", Schweizerische Medizinische Wochenschrift—Journal Suisse de Medecine, vol. 87, Supplement for No. 24, pp. 739-748, 1957.

K. Sigg, "New Approaches to the Treatment of Thrombosis", Angiology—The Journal of Vascular Diseases, vol. 8, No. 1, pp. 44-59, Feb. 1957.

K. Sigg et al., "Prophylaxis of Thrombosis during Gravidity", Die Medizinische, No. 12, pp. 420-423, Jan. 1957.

B. Gyorgy, "Visszérbetegség Másodlagos Szövödményeinek Kelelése", Orvosi Hetilap, vol. XCIX, No. 35, pp. 1215-1218, 1958.

Dr. Hermann Rompp; "Varsyl"; Chemie Lexikon, Vierte Vollig Neu Bearbeitete Auflage; p. 4649 ; 1958.

F. Jaeger, "Varcose Veins", Deutsche Medizinische Wochenschrift, vol. 83, No. 30, p. 1295, Jul. 1958.

K. Sigg, "Prevention and Treatment of Thromboembolic Complications", Wiener Medizinische Wochenschrift, No. 10, pp. 206-213, Mar. 1958.

E. Rapped, "The achievements of surgical therapy of varicose veins and leg ulcers?", Die Medizinische, No. 22. pp. 906-914, May 1958.

E.J. Orbach, "Has Injection Treatment of Varicose Veins Become Obsolete?", The Journal of American Medical Association, vol. 166., No. 16, pp. 1964-1966, Apr. 19, 1958.

A. Lemaire et al., "Effect of Intra-arterial oxygen injection on blood cholesterol", Therapie, vol. 13, pp. 395-399, 1958.

69$^{th}$ Medical Seminar Evening of the Van-Swieten Society in the District Hospital of Villach, pp. 1-2, Meeting of Oct. 30, 1959.

A. Ree; "The Treatment of Varicose Veins with Etamolin Foam"; Acta Dermato-Venereologica; vol. 39, pp. 428-432; 1959.

H. Dodd, "Varicose Veins and Venous Disorders of the Lower Limb", The Irish Journal of Medicinal Science, Sixth Series, No. 400, pp. 162-174, Apr. 1959.

A. I. S. MacPherson, "The Treatment of Varicose Veins", The Practitioner—Diseases of the Veins, vol. 183, No. 1093, pp. 11-18, Jul. 1959.

F.R. Methiesen, "Subclinical Deep Venous Damage After Sclerosing Injection Demonstrated by Phlebography", Acta Chirurgica Scandinavica, vol. 118, Fasc. 2, pp. 155-166, 1959.

C. Olivier, "Surgical Treatment of Trophic Ulcers of the Inferior Members", Journal de Chirurgie, vol. 78, No. 2, pp. 157-174, Oct. 1959.

K.R. Ramstad et al., "Operative Treatment of Varicose Veins—Follow-up of Patients Treated with ligature/injection and "Stripping" respectively", Tidsskrift for Den Norske Laegeforening, No. 10, pp. 623-625, May 1959.

V. Gorisch et al., "Expiration of labeled oxygen after intravenous insufflation", Medicina Experimentalis, vol. 1, pp. 333-338, 1959.

H. Dodd, "Vulval Varicose Veins in Pregnancy", Tensile Strength of Arterial Grafts, British Medical Journal, pp. 831-832, Mar. 28, 1959.

I. Berson, "Sclerotization or surgery in the treatment of varicose veins of the inferior extremities", University Clinic for dermato-venerology, Lausanne, pp. 485-190, 1960.

J. Marmasse, "Sclerosing Injections in the Saphenofemoral Junction of the Saphenous Veins. Exploration, Injection, Critique.", La Semaine des Hopitaux, vol. 36, No. 17, pp. 1086-1095, Apr. 1960.

F.R. Mathiesen, "Treatment of Varicose Veins—Retrograde Injection or Communicant Resection", Nordisk Medicin, vol. 64, No. 48, pp. 1525-1529, 1960.

P. Sicard, "Sclerosing Treatment of Varicose Veins of the Lower Limbs", Therapeutics, vol. 36, No. 2, pp. 127-129, Feb. 1960.

W. Stern, "Varicose Veins", The Medical Journal of Australia, vol. II, No. 18, pp. 849-852, Oct. 29, 1960.

F. Voss, "Special Methods in the Sclerotherapy of Venous Leg Maladies", Zeitschrift für Haut-und Geschlechts-Krankheiten, vol. XXVII, No. 9, pp. 304-306, 1960.

W.G. Fegan, "Continuous Uninterrupted Compression Technique of Injecting Varicose Veins", Proceedings of the Royal Society of Medicine, vol. 53, No. 7, pp. 837-840, Jul. 1960.

V. Gorisch et al., "Appearance of intravenously given radioactive oxygen in expired air", Naunyn-Schmiedebergs Archiv fuer Experimentelle Pathologie und Pharmakologie, vol. 238, pp. 106-107, 1960.

K. Sigg et al., "New Sclerosing Substances for Varicose Veins", Munchener Medizinische Wochenschrift, Issue 1, Mar. 1961.

J.T. Hobbs, "The Treatment of Varicose Veins in Dublin", Clinical Supplement, pp. 57-60, 1961.

A. Wiedmann, "The Varicose Symptom Complex", Report on the Literature from the years 1955-1960, Part 1, Varices, Der Hautarzt, vol. 12, No. 9, pp. 385-391, Sep. 1961.

Von A. Wiedmann, "Varicose Veins", Der Hautarzt, Year 12, No. 10, pp. 433-438, Oct. 1961.

E. Günther, "On the indication and method of sclerotherapy", Ärztliche Fortbildung, vol. 55, Brochure 22, pp. 1296-1298, Nov. 1961.

R. Rauhs, "Sclerotherapy, its indications and treatment successes", Klinische Medizin, Issue 1, pp. 5-12, Jan. 1961.

W. Scneider, "Regarding non-operative varicosclerosation", Die Medizinische Welt, vol. 3, No. 5, pp. 225-227, Feb. 1961.

K. Sigg, "Treatment of Varices, varicose ulcer and thrombosis", Vienna Medical Weekly Journal, No. 6, Feb. 11, 1961.

L. Gerson, "The Treatment of Varicose Veins, A Critical Study of Choice of Method", Angiology, The Journal of Vascular Diseases, vol. 13, No. 16, pp. 260-264, 1962.

W. Maurer, "Is the sclerosing therapy in the case of varicosis advisable in practice?", Therapie der Gegenwart, Issue 5, pp. 242-245, May 1961.

J.P. Medelman, "History of the Section on Radiology", The Journal of the American Medical Association, vol. 178, No. 8, pp. 785-911, Nov. 25, 1961.

H. Dodd, "Varicose Veins and Venous Disorders of the Lower Limb", The Proceedings of the Cardiff Medical Society, pp. 28-45, 1962.

H.O. Schneider, "Varix Treatment with Modern Sclerosing Agent", Zeitschrift für Haut und Geschelchtskrankheiten, Band XXXIII, Heft No. 5, pp. 163-166, Sep. 1962.

I. Singh, "Life Without Breathing", Arch. int. Pharmacodyn., vol. CXXXVII, No. 3-4, pp. 318-330, 1962.

P. Flückiger et al., "Physical and Biological Pathogenetic Components of Varicosis", Schweizer Medizinische Wochenschrift, No. 45, 1963.

E.J. Orbach, "Misconceptions and Pitfalls in Sclerosing Therapy of Varicose Veins", Angiology—The Journal of Vascular Diseases, vol. 14, No. 11, pp. 552-555, Nov. 1963.

O. Gilje, "Injection Treatment of Varicose Veins", Den norske Legeforening, No. 17, pp. 1380-1381, Sep. 1963 and translation into English.

J.C. Luke et al., "Factors in the Improvement of Results in Varicose Vein Surgery", Improved Vein Surgery, Canadian Journal of Surgery, vol. 6, No. 2, pp. 145-148, Apr. 1963.

K. Sigg, "Varicosis and Thrombosis during Pregnancy, birth and in childbed", Zentralblatt für Gynäkologie, No. 8, pp. 254-259, Feb. 23, 1963.

E.C. Emerson, "A Reappaisal of the Injection Treatment of Varicose Veins", Angiology The Journal of Vascular Diseases, vol. 14, No. 1, pp. 8-13, Jan. 1963.

P. Flückiger et al., "A Contribution to the Techniques for Outpatient Treatment of Varicose Veins", Lecture delivered at the meeting of the German Working Group on Phlebology and the Hamburg Dermatological society on Oct. 20, 1962, Med. Welt 1963, No. 12, pp. 617-621.

I.M. Aizman, "On the Treatment with Sclerosal Agents of Patients with Varicose Lower Extremities", Xupyprus, pp. 46-49, 1964.

M. Fabi et al., "Un Nuovo Metodo Di Terapia Sclerosante nel Trattamento Delle Varici", L'Arcispedale S. Anna di Ferrera, Book 1, pp. 351-354, 1964.

W.G. Fegan et al., "A Modern approach to the injection treatment of varicose veins and its applications in pregnant patients", American Heart Journal, vol. 68, No. 4, pp. 757-764, Oct. 1964.

H.J. Leu et al., "The Modern Conception of Therapy of Varicose Veins", Angiology, The Journal of Vascular Diseases, vol. 15, No. 9, pp. 371-378, Sep. 1964.

E.J. Orbach, "A Unified Approach to the Therapy of Varicosities", Angiology, vol. 15, No. 12, pp. 558-560, Dec. 1964.

R. Santler, "Sclerosing Therapy of Varicose Veins", Weiner Klinische Wochenschrift, Issue 24, No. 76, pp. 431-4.34, Jun. 12, 1964.

W. Schneider et al., "On the histology of the Varicose Injection Treatment in People with new Injection Treatment Agents", Archive for Clinical and Experimental Dermatology, vol. 220, pp. 234-249, 1964.

K. Sigg, "Treatment of Varicose Veins in 2-5 days", Dermatologica, vol. 129, No. 2, pp. 111-117, 1964.

K. Sigg, "La Profilassi e la terapia delle malattie venose degli arti inferiori mediante la compressione con fasciature e con calze elastiche", Minerva Ginecologica, vol. 16, No. 19, pp. 817-823, Oct. 15, 1964.

E.J. Orbach, "Article on Treatment of Teleangiectasias", Zentralblatt für Phlebologie, Heft 1, Band 3, pp. 4-7, Feb. 15, 1964.

Von H. Pfosi, "On the Sclerosing Treatment of Varicose Veins", Schweizerische Rundschau für Medizin—Revue Suisse de medecine, 54$^{th}$ year of Edition, No. 29, pp. 868-871, Jul. 22, 1965.

K. Sigg, "Varicose Vein Therapy", Deutsche MEdizinische Wochenschrift, No. 15, pp. 665-666, Apr. 9, 1965.

R. Tournay, Indication of the Exclusive Sclerotherapy or the Consecutive Combination Therapy Surgery-Sclerotization of Varicose Veins, Zentralblatt für Phlebologie, vol. 4, No. 1, pp. 133-142, Feb. 15, 1965.

E. J. Orbach, "The Place of Injection Therapy in the Treatment of Venous Disorders of the Lower Extremity—with Comments on its Technique", Presented at the Annual Meeting of the International College of Angiology, London, pp. 18-23, Jul. 1965.

C. Olivier et al., "Reinterventions Performed on Primary Varicose Veins of the Lower Limbs", La Presse Medicale, vol. 74, No. 26, pp. 1355-1360, May 25, 1966.

E.J. Orbach, "The Place of Injection Therapy In the Treatment of Venous Disorders of the Lower Extremity—with Comments on its Technique", Angiology—The Journal of Vascular Diseases, vol. 17, No. 1, pp. 18-23, Jan. 1966.

G. Fegan, "The Treatment of Venous Insufficiency During Pregnancy", Varicose Veins—Compression Sclerotherapy, Chapter VII, pp. 93-98, 1967.

M.D.H.-D. Bock; "Varicosis and its Therapy"; Ärztliche Praxis; XIX Volume, No. 60, pp. 2146-2148; Jul. 29, 1967.

P. Flückiger, "Intraoperative Varicosclerosation with Sodium Tetradecyl Foam in the Babcock Operation", Zentralblatt für Phlebologie, Heft 1, Band 6, pp. 514-518, Feb. 1967.

K. Sigg, "Sclerotherapy in the Treatment of Varicose Veins", Internist, pp. 388-398, 1967.

Dr. E. Lunkenheimer; letter to Chem. Fabrik Kreussler & Co.; Mar. 20, 1967.

B. Ya Varshayskii, "Mechanism of Changes in Renal Activity Following intravenous oxygen", vol. 53, No. 2, pp. 173-177, 1967.

O. Henschel;"Die Varizenverördening—Verördungstherapie mit Aethoxysklerol—Kreussler"; p. 22; 1968.

W.K. Blenkinsopp, "Effect of Injected Sclerosant (Tetradecyl Sulphate of Sodium) on Rat Veins", Angiologica, vol. 5, No. 6, pp. 386-396, 1968.

E. Frugis et al., "Telangieceasia Sclerotherapy of the Lower Limbs", Minerva Dermatologica, Vo. 43, pp. 368-371, 1968.

J. Orbach, "Varicose Veins", Medical Trial Technique Quarterly, vol. XIV, No. 4, pp. 27-38, Jun. 1968.

J. Steinacher et al., "Path and Retention Time of a Contrast Medium in the Superficial Venous System under the Conditions of Varix Obliteration. A Study on the method of varix obliteration", Zsch. Haut-Geschl. vol. 43, No. 9, pp. 369-376, 1968.

J.T. Hobbs, "The Treatment of Varicose Veins—A Random Trial of Injection-Compression Therapy Versus Surgery", Brit. J. Surg., vol. 55, No. 10, pp. 777-780, Oct. 1968.

H. Eichenberger, "Results of the Sclerotherapy of Varicose Veins with Hydroxypolyaethoxy-Dodecan", Zentralblatt für Phlebologie, vol. 8, pp. 181-183, 1969.

K. Sigg, "Phlebosclerosation: experience and results", Der Chirurg, vol. II, No. 40, pp. 487-491, 1969.

W. Gillesberger; "The Equipment of the Dermatologist Working in the Field of Phlebology", The Journal for Skin Diseases; vol. 44 (18), pp. 669-674; 1969.

B. Stemmer et al., Phlebologie, vol. 22, No. 2, pp. 151-172, Apr.-Jun. 1969.

G. Wesener, "Morphology and new therapies for starburst varicosis and essential telangiectasia", Berufs-Dermatosen, vol. 17, No. 5, pp. 273-281, Oct. 1969.

W.K. Blenkinsopp, "Choice of Sclerosant: An Experimental Study", Angiologica, vol. 7, No. 3, pp. 182-186, 1970.

K. Holzegel, "On Sclerosing Agents for Varicose Veins", Zentralblatt für Phlebologie, vol. 9, pp. 43-53, 1970.

B. Stemmer, "Comparison of Common Sclerosing Techniques", Zentralblatt für Phlebologie, vol. 3, pp. 170-176, 1970.

J. Edmonds-Seal et al., "Air Embolism", Anaesthesia, vol. 26, No. 2, pp. 202-208, Apr. 1971.

H.J. Leu et al., "The Combined Surgical-Sclerotic Ambulatory Treatment of Saphenous Varicose Veins", Schweizerische Rundschau für Medizin, vol. 1, No. 61, pp. 1360-1364, Oct. 31, 1972.

K. Sigg, "Technical Details about Injecting Varices", Med. Klin., vol. 67, No. 27/28, pp. 955-959, 1972.

Z. Salamon, "Sclerosing Agents—Toxicity and Mechanism of Action", Wiadomosci Lekarskie, vol. 26 (19), pp. 1819-1822, 1973.

W.G. Fegan, "Conservative Treatment of Varicose Veins", Progr. Surg. vol. 11, pp. 37-45, 1973.

P. Flückiger, "Der Erythem-Test im Rahmen der praoperativen Varizenuntersuchung", Präktische Hinweise-Practical Advice, vol. 3, No. 2, pp. 198-199, 1974.

S. Efuin et al., "Oxygen Parameters of Blood and Tissues during Intravascular Oxygenation of the Organism", Eksperimental'naya Khirurgiya I Anesteziologiya, vol. 5, pp. 183-186, 1974.

E.J. Orbach, "The importance of removal of postinjection coagula during the course of sclerotherapy of varicose veins", VASA, vol. 3, No. 4, pp. 475-477, 1974.

Malyugin, "Influence exerted on the liver by the intraportal administration of oxygen", Farmakologiya, vol. 37, No. 2, pp. 183-186, 1974.

J.T. Hobbs, "Surgery and Sclerotherapy in the Treatment of Varicose Veins", Arch. Surg. vol. 109, pp. 793-796, Dec. 1974.

E.J. Orbach et al., "Investigation of the Different Injection Techniques in the Sclerotherapy of Varicose Veins by Minidose and Differential Pressure Phlebography", VASA, vol. 4, No. 2, pp. 175-183, 1975.

K. Sigg, "Quick Treatment—a modified Method of Sclerotherapy of Varicose Veins", Zur Diskussion gestellt—Open for Discussion, VASA, vol. 4, No. 1, pp. 73-78, 1975.

H.L. Myers, "Injection Therapy for Varicose Veins", The Journal of Family Practice, vol. 3, No. 5, pp. 531-534, 1976.

E.J. Orbach, "Controversies and Realities of Therapy for Varicosis", International Surgery, vol. 62, No. 3, pp. 149-151, Mar. 1977.

J. Hobbs, "Surgery or Sclerotherapy for Varicose Veins", Archs. Surg. Nol. 109, p. 793, 1974.

P. Ouvry et al., "Aétoxisclerol: First Impressions", Phlébologie, vol. 31, No. 2, pp. 75-77, 1978.

D. Reinharez, "Perforating Vein Sclerosis Technique", Ph Phlébologie, vol. 31, No. 2, pp. 69-74, 1978.

K. Sigg et al., "Treating varices with Sclerotherapy", Langenbacks Arch. Chir., vol. 347, pp. 231-234, 1978.

E.J. Orbach, "Hazards of Sclerotherapy of Varicose Veins—their prevention and treatment of complications", VASA, vol. 8, No. 2, pp. 170-173, 1979.

P. Ouvry et al., "Sclerosant Treatment of Telangiectasias of the Lower Limbs", Phlébologie, vol. 32, No. 4, pp. 365-370, 1979.

P. Ouvry et al., "Le Traitement Sclérosant des Télangiectasies des Membres Inférieurs", Phlébologie, vol. 35, No. 1, pp. 349-359, 1982.

E.L. Bodian, "Techniques of Sclerotherapy for Sunburst Venous Blemishes", J. Dermatol. Surg. Oncol. vol. 11, No. 7, pp. 696-704, Jul. 1985.

D.S. Camara et al., "The Hemodynamic Effects of the Sclerosant Sodium Morrhuate in Dogs", Surgery—Gynecology and Obstetrics, vol. 161, No. 4, pp. 327-331, Oct. 1985.

A. Davy et al., "Ostial Incompetence—Sclerosis or Resection?", Phlébologie, vol. 39, No. 1, pp. 35-45, 1986.

F.B. Cockett, "Arterial Complications during Surgery and Sclerotherapy of Varicose Veins", Phlebology, vol. 1, pp. 3-6, 1986.

M.P. Goldman et al., "Continuing Medical Education (Dermatologic Surgery), Treatment of Telangiectasia: A review", Journal of the American Academt of Dermatology, vol. 17, No. 2, part 1, pp. 167-182, Aug. 1987.

E. Morsiani et al., "Effect of Intravenous and Intreperivenous Injections of Sclerosants (Sodium Tetradecyl Sulfate and Hydroxy Polyethoxy Dodecan) on the Rat Femoral Vein", Resesarch in Experimental Medicine, vol. 187, pp. 439-449, 1987.

P. Ouvry et al., "Sclerotherapy of Perforating Veins", Phlébologie, vol. 40, No. 3, pp. 633-641, 1987.

Karmazsin et al., "Experimental Study of Lipid Peroxidation Following Intravenous Oxygen", Kiserletes Orvostudomany, vol. 39, pp. 342-348, 1987.

J.T. Hobbs, "Compression Sclerotherapy in Venous Insufficiency", Acta Chir Scand Suppl., vol. 544, pp. 75-80, 1988.

Dr. Med. Jože Baridevic; "Varicosclerozation in Phlebological Practice"; The Journal for Doctors, in Clinic and Practice; XXI vol. No. 3, pp. 126-136; Jan. 11, 1989.

W. DeGroot et al., "Treatment of Varicose Veins: Modern Concepts and Methods", The Journal of Dermatologic Surgery and Oncology, vol. 15, No. 2, pp. 191-198, Feb. 1989.

M.A. Farina et al., "Outpatient Treatment of Varicose Vein Segments: Two Techniques Compared", Phlébologie, pp. 1070-1071, 1989.

D. Gasparini, "Therapeutic Embolization in Pulmonary Hemorrhage", Radiologica Interventistica, vol. 77, pp. 223-229, 1989.

G. Hauer, "Diagnostic and Surgical Treatment of Varicose Veins", Herz, vol. 14, No. 5, pp. 274-282, 1989.

K.M. Hördegen, "Conconitant Circulatory Problems in the Arteries or immobility in mostly older patients make outpatient treatment of ulcers more difficult", Schweiz. Med. Wschr., vol. 119, No. 37, pp. 1264-1269, 1989.

P.A. Ouvry, "Telangiectasia and Sclerotherapy", J. Dermatol. Surg. Oncoo. vol. 15, No. 2, pp. 177-181, Feb. 1989.

R.M. Knight et al., "Ultrasonic Guidance of Injections into the Superficial Venous System", Phlebology, pp. 339-341, 1989.

S.N. Vasdekis et al., "Evaluation of non-invasive and invasive methods in the assessment of short saphenous vein termination", Br. J. Surg., vol. 76, pp. 929-932, 1989.

M. Masaki et al., "The destructive effects of sclerosant ethanolamine oleate on mammalian vessel endothelium", Gastroenterologia Japanica, vol. 25, No. 1, pp. 230-235, Feb. 1990.

Z.B. Shafi et al., "Factors Affecting High Shear Preparation of Albumin Microspheres", Pharmaceutical Sciences Research Group, p. 144P, 1990.

N. Weindorf et al., "Control of Sclerosis—Treatment for Varicose Veins", Phlébologie, vol. 43, No. 4, pp. 681-689, 1990.

M.P. Goldman, M.D. "Variations on Injection Technique", Sclerotherapy: Treatment of Varicose and Telangiectatic Leg Veins, pp. 274-275, 290, 312-323, 1991.

G. Belcaro et al., "Treatment of Superficial Venous Incompetence with the Savas Technique", Journal des Maladies Vasculaires (Paris), vol. 16, pp. 23-27, 1991.

H.R. Bernbach, "Sclerosing Injections Using the Sigg Method", Phlébologie, vol. 44, No. 1, pp. 31-36, 1991.

Y.A. Ershov et al., "Variant of an Operation on Enlarged Veins of the Oesophagus and Cardia in Patients with Portal Hypertension Syndrome", Surgery—Monthly Science Practice Journal, Ministry of Health of the Union of Soviet Socialist Republics All-Union Scientific Society of Surgeons, pp. 46-49, Sep. 9, 1991.

M.P. Goldman, "Sclerotherapy Treatment of Varicose and Telangiectatic Leg Veins", Clinical Methods for Sclerotherapy of Varicose Veins, pp. 274-275, 290, 312 and 323, 1991.

J.T. Hobbs, "Varicose Veins", ABC of Vascular Diseases, vol. 303, pp. 707-710, Sep. 21, 1991.

F. Vin, "Echo-Sclerotherapy of the Small Saphenous Vein", Phlébologie, vol. 44, No. 1, pp. 79-84, 1991.

G. Miserey et al., "Sclerose Sous Echographie Dans Certaines Zones a Risques", Phlébologie, vol. 44, No. 1, pp. 85-96, 1991.

M. Schadeck et al., "Echotomographie de la Sclerose", Phlebologie, vol. 44, No. 1, pp. 111-130, 1991.

R. de Somer-Leroy et al., "Echographie du Creux Poplite Recherche D'Une Arteriole Petite Saphene Avant Sclerotherapie", Phlébologie, vol. 44, No. 1, pp. 69-78, 1991.

G. Belcaro et al., "Treatment of Superficial Venous Incompetence with a Hemodynamic Technique on an Outpatient Basis: The SAVAS Technique", Vascular Surgery, pp. 32-36, Jan./Feb. 1992.

R. Muller, "The Ambulatory Phlebectomy", Therapeutische Umschau, vol. 49, No. 7, pp. 447-450, 1992.

P. Thibault et al., "Recurrent Varicose Veins", Phlebology, vol. 18, pp. 895-900, 1992.

G.J. Postma, "Ethanolamine Oleate Injection: Therapeutic and Pharmaceutical Aspects", Journal of the Dutch Association of Hospital Pharmacists, 8th year, Issue 3, pp. 84-91, Sep. 1992.

M. Schadeck, "Sclerotherapy in the Child", Phlébologie, vol. 45, No. 4, pp. 509-512, 1992.

M. Schadeck; "Ultrasound-controlled Sclerotherapy of the Great Saphenous Veins"; Phlébologie; vol. 46, No. 4, pp. 673-682, 1993.

K. Biegeleisen et al., "Inadvertent Intra-Arterial Injection Complicating Ordinary and Ultrasound-Guided Sclerotherapy", Phlebology, vol. 19, pp. 953-958, 1993.

M. Schadeck; "Duplex Controlled Sclerosing Treatment of the Great Saphenous Vein"; Phlebol; vol. 25, pp. 78-82; 1996.

Craig F. Feied, MD, FACEP; "Treatment of all Sizes of Varicose Veins and Spider Veins for Healthy, Beautiful Legs. Mechanism of Action of Sclerosing Agents and Rationale for Selection of a Sclerosing solution"; American Vein Institue; 1996.

"Sulfaproxyline"; The Merck Index, an Encyclopedia of Chemicals, Drugs, and Biologicals, 12th Edition; p. 1527; 1996.

J.R. Cabrera et al.; "Extending the Limits of Sclerotherapy: New Sclerosing Products"; Phlébologie; 50 No. 2; pp. 181-188; 1997.

J. Cabrera Garrido et al. ; "Elargissement de Limites de la Sclérothérapie: Nouveaux Proits Sclérosants"; Phlébologie; vol. 50, No. 2 ; pp. 181-188 ; 1997.

J. Garcia Mingo, "Venous Sclerosis with Foam 'Foam Medical System'", Revista Española de Medicina y Ciruia Cosmética, vol. 7, pp. 29-31, 1999.

Robert J. Min; "Transcatheter Duplex Ultrasound Guided Sclerotherapy"; Abstracts from the 13th Annual Congress of the American College of Phlebology; Nov. 10-13, 1999.

J. Cabrera Garrido et al.;"Escleroterapia en Micorespuma : Nuevo Concepto en Escleroterapia. Resultados a Lorgo Plazo."; Revista Panamericana de Flebologia y Lonfologia; No. 34; pp. 29-37; Sep. 1999.

A. Cavezzi, "The Use of Sclerosant Foam in Sclerotherapy: possibilities and limits", Management of Venous Disease in the New Millennium, pp. 16-17, Jul. 2000.

J. Cabrera et al. ;"Treatment of Varicose Long Saphenous Veins with Sclerosant in Microfoam Form: Long-Term Outcomes"; Phlebology; No. 15, pp. 19-23; 2000.

E. Rabe et al.; "Guidelines to Sclerosing Treatment of Varicose Veins"; Leitlinien der DGP, Phlebologie; vol. 6, pp. 154-158; 2001.

D. Goldberg ;"Nd : YAG Laser Treatment of Spider Veins"; pp. 284-288.

A. Frullini; "Sclerosing Foam with Polidocanol or Sodium Tertradecyl Sulphate in the Treatment of Superficial Venous Insuffiency"; pp. 289-292.

J. Cabrera et al.; "Treatment of Varicose Long Saphenous Veins with Sclerosant in Microfoam Form: Long-Term Outcomes"; pp. 293-298.

F. Heinrich; "Venous Thrombosis and Pulmonary Embolism during Pregnancy and the Puerperium"; pp. 299-308.

F.X. Breu et al.;"Duplex Scanning of Lipedema and Lymphedema"; pp. 309-320; Scope on Phlebology and lymphology; vol. 8; Issue 3/4; Dec. 2001.

Gianni Belcaro; "Micro-sclerotherapy"; Sclerotherapy in Venous Disease; pp. 89-95; 2002.

A. Frullini et al., "Sclerosing Foam in the Treatment of Varicose Veins and Telangiectases: History and Analysis of Safety and Complications", Dermatol Surg. vol. 28, No. 1, pp. 11-15, Jan. 2002.

P. Coleridge Smith, "Foam Sclerotherapy in Treatment of Varicose Veins: Results from Europe", Invited Presentation at Pacific Vascular Symposium, Kona, Nov. 2002.

A. Cavezzi et al., "Treatment of Varicose Veins by Foam Sclerotherapy: Two Clinical Series", The Venous Forum of the Royal Society of Medicine and Societas Phlebologica Scandinavika, vol. 17, No. 1, pp. 13-18, Nov. 2002.

Butler Studies to Date, "Summary of the Butler gas physiology studies to date (Jun. 13, 2003)", pp. 1-12.

Syllabus & Scientific Abstracts of the UIP World Congress Chapter Meeting, San Diego, California, Aug. 27-31, 2003.

Dr. J.C. Wollmann et al.; Evaluation of the Test; Kreussler Pharma; pp. 17-28, Jan. 29, 2003.

C. Frullini, et al., "Personal Experience with the Sclerosing Foam in Duplex Guided Sclerotherapy", pp. 1-4.

"Phlebocid"; CSST—Service du Répertoire Toxicologique; Case No. 2272-11-9; http://www.reptox.csst.

J. Cabrera; "Application Techniques for Sclerosant in Micro-Foam Form"; pp. 39-44.

Pr. Dr. R. Höhler ; "The Indication of the Rotation Speed and the Duration of the Rotation is not Sufficient for Foams Produced by a Rotating Brush to be Able to Produce a Foam that Has Well-Defined Properties and that Can Be Reproduced."

A. Frullini; "Sclerosing Foam in the Treatment of Recurrent Varicose Veins"; Foam Sclerotherapy—State of Art; pp. 73-77.
"The F2 Finger Pump Foamer," Airspray.
Cabrera-Garrido, et al., "New Sclerosing Products: Extending limits in Sclerotherapy," Phlebologie, 50 No. 2, p. 181-188, 1997.
Minga, Javier Garcia, "Venous sclerotherapy with foam: 'Foam Medical System'," p. 1-3, 1999.
Garrido, Jesús, "Medicine: Microfoam sclerosants against venous illnesses," Medical News, p. 12-16, May 1997.
Baniel, A. et al., "Foaming Properties of Egg Albumen with a Bubbling Apparatus compared with Whipping," J. Food Science, vol. 62(2): 377-381, 1997.
Eurospray—Examples of refillable air powered containers.
Eurospray—Pictures of Eurospray devices, No. 1.
Eurospray—Pictures of Eurospray devices, No. 2.
Eurospray—Pictures of Eurospray devices, No. 3.
Eurospray—Pictures of Eurospray devices, No. 4.
Eurospray—Pictures of Eurospray devices, No. 5.
Eurospray—Pictures of Eurospray devices, No. 6.
Eurospray—Pictures of Eurospray devices, No. 7.
Eurospray—Pictures of Eurospray devices, No. 8.
Eurospray—Pictures of Eurospray devices, No. 9.
Eurospray—Pictures of Eurospray devices, No. 10.
British Technology Group, Leaflet on Atmosol—"The Atmosol Regulator," The Atmosol System.
British Technology Group, Leaflet on Atmosol—The Acceptable Aerosol System.
Cabrera-Garrido, J, et al. "New Pharmaceutical Form of Sclerosants: Use in the Treatment of Inoperable Venous Malformations," Poster, May 1997.
The Airspray Foamer Components.
English translation of Cabrera-Garrido, J.R. & J.R. Cabrera Garcia-Olmedo, "New Method of Effecting Sclerosis in Varices of the Trunk Veins" Vascular Pathology, vol. 1, No. 4, Oct. 1995.
Frullini, A "Foam Sclerotherapy: a review" Phlebolymphology, No. 40, p. 125-129, 2003.
Bergan, J., "Classic Paper: Nicht-Operative Varizenverodung Mit Varsylschaum," Abstract, Venous digest, 2006.
Grondin, L., "Echosclerotherapy of Saphenous Axis with Microfoam Agents," Abstracts form the $13^{th}$ Annual Congress of the American College of Phlebology, Nov. 1999.
Wollmann, J., "The History of Sclerosing Foams" Dermatol. Surg. 2004; 30:694-703.
English translation of Opposition to the European Patent EP 1 180 015 B1, filed Sep. 21, 2006.
English translation of Höhler, R., "The term 'Microfoam' is neither generally known nor well defined in the specialist World".
Hess, H., "Digital Subtraction Arteriography with Carbon Dioxide: an alternative to arteriography of the extremities with iodine-containing contrast media," Forlschr. Röntgenstr., 1990, 153(3): 233-238.
König, T. & Krasmy, R., "CO2 Angiography: Measurement of vascular gas filing and evaluation of parameters influencing gas injection using a circulatory system model," Biomedizinische Technik, 1991, 34(11): 266-270.
Grosse-Brockhoff, F. et al., "Carbon Dioxide as a Contrast Medium for use in Radiology of the Heart and Blood Vessels," Fortschritte Auf Dem Gebiete Der Räntgenstrahlen Und Der Nuklearmedizin, 1957, 86(3): 285-291.
Seeger, J., et al., "Carbon Dioxide Gas as an Arterial Contrast Agent," Annals of Surgery, vol. 217, No. 6, p. 688-698, 1993.
Nullity Appellant's statement dated Apr. 4, 2007 in German Nullity Appeal Proceedings BTG International Ltd., 114-59/03.
Definition of Caisson disease.
Graff, T. et al., "Gas Embolism: A Comparative Study of Air and Carbon Dioxide as Embolic Agents in the Systemic Venous System" Am. J. Obst. & Gynec., Aug. 1959 p. 259-265.
Steffey, E. et al., "Nitrous Oxide Intensifies the Pulmonary Arterial Pressure Response to Venous Injection of Carbon Dioxide in the Dog" Anesthesiology 52: 52-55, 1980.
Moore, R.M. and C.W. Braselton, "Injections of Air and of Carbon Dioxide into a Pulmonary Vein" Annuals of Surgery, Aug. 1940 p. 212-218.
Wollmann, J. "60 years of Sclerosing Foam" Phlebologie 2, p. 63-70, 2004.
Judgment dated May 22, 2007, in German Nullity Appeal Proceedings BTG International Ltd., X ZR 56/03.
Cabrera, J., "Sclerosants in Microfoam," International Angiology, 2001, 322-329.
Frullini, A., "New Technique in Producing Sclerosing Foam in a Disposable Syringe," Dermatol. Surg., 2000, 26, 705-706.
Tessari, L., "Preliminary Experience with a new Sclerosing Foam in the Treatment of Varicose Veins," Dermatol. Surg., 2001, 27, 58-60.
Wright, David, Presentation, "The Varisolve® Trial Will Foam Make EVLA and RFA obsolete?" (2008).
Elias, Steve, "Is There A Leak? Where Is the Leak? How Many Leaks? Which Leak Do I Fix?," American College of Phlebology, Marcoisland Nov. 7-9, 2008.
Rathbun, Suman, "Venous Thromboembolism: The Problem," American College of Phlebology, Marcoisland Nov. 7-9, 2008.
Pittalugap, Paul, "The Complex Case," American College of Phlebology, Marcoisland Nov. 7-9, 2008.
Wakefield, Thomas, "Diagnosis and Management of PE," American College of Phlebology, Marcoisland Nov. 7-9, 2008.
Guex, J-Jerome, "The French Polidocanol Registry on Long Term Side Effects: A Survey Covering 3357 Patient Years," American College of Phlebology, Marcoisland Nov. 7-9, 2008.
Fronek, Helane, "Treatment of Small Veins," American College of Phlebology, Marcoisland Nov. 7-9, 2008.
Schul, Marlin, "Compression Therapy vs. Sclerotherapy for Isolated Refluxing Reticular Veins and Telangiectasia: 12 Month Results of a Randomized Trial," American College of Phlebology, Marcoisland Nov. 7-9, 2008.
Schliephake, Dorothee, "A New Standard Digital Imaging System to Document Treatment Success After Sclerotherapy of C1 Varicose Veins Applied in a Double-Blind, Randomized, Controlled Clinical Trial (EASI Study)," American College of Phlebology, Marcoisland Nov. 7-9, 2008.
Wright, David, "A Single Center Pilot Study of Polidocanol Endovenous Microfoam (PEM) Treatment to Evaluate Presence and Durability of Gas Emboli Using Echocardiography," American College of Phlebology, Marcoisland Nov. 7-9, 2008.
Comerota, Anthony, "Management of Acute DVT," American College of Phlebology Marcoisland Nov. 7-9, 2008.
Stoughton, Julianne, "Basic Sclerotherapy," American College of Phlebology, Marcoisland Nov. 7-9, 2008.
Hill, Douglas, "Comparison of Sclerosant Foam Stability by Foam Composition," American College of Phlebology, Marcoisland Nov. 7-9, 2008.
Morrison, Nick, "Foam Safety Studies," American College of Phlebology, Marcoisland Nov. 7-9, 2008.
Rabe, Eberhard, "Polidocanol, Sodium Tetradecyl Sulfate and Placebo for Sclerotherapy of C1-Varicose Veins," American College of Phlebology, Marcoisland Nov. 7-9, 2008.
Gibson, Kathleen, "Proprietary Polidocanol Endovenous Microfoam Bubble Embolization Does Not Cause Cerebral Injury," American College of Phlebology, Marcoisland Nov. 7-9, 2008.
Slutsky, Eileen, "Sclerotherapy Complications Matting, Staining and Lack of Improvements," American College of Phlebology, Marcoisland Nov. 7-9, 2008.
Gillet, Jl, "Side Effects and Complications of Foam Sclerotherapy of the Great and Small Saphenous Veins: a Controlled and Multicentre Prospective Study Including 1025 Patients," American College of Phlebology, Marcoisland Nov. 7-9, 2008.
Morrison, Nick, "Strategies for Preventing the Big, Bad Complications," American College of Phlebology, Marcoisland Nov. 7-9, 2008.
Krusch, Michael, "Insurance and Coding for the Phlebology Practice," American College of Phlebology, Marcoisland Nov. 7-9, 2008.
Caprini, Joseph, "Direct Factor X Inhibition," American College of Phlebology, Marcoisland Nov. 7-9, 2008.
Caprini, Joseph, "DVT Prophylaxis: What Every Physician Should Know," American College of Phlebology, Marcoisland Nov. 7-9, 2008.

Neuhardt, Diana, "Emboli Detection in the MCA Concurrent With Treatment of LE Superficial Venous Insufficiency with Foam Sclerotherapy," American College of Phlebology, Marcoisland Nov. 7-9, 2008.
King, Ted, "Off Label and/or Non-FDA Approved Drugs," American College of Phlebology, Marcoisland Nov. 7-9, 2008.
Frullini, Alessandro, "Sclerosing Foam," American College of Phlebology, Marcoisland Nov. 7-9, 2008.
Meissner, Mark, "Pelvic Veins and Vascular Malformation," American College of Phlebology, Marcoisland Nov. 7-9, 2008.
Schul, Marlin, "Insurance Denials," American College of Phlebology, Marcoisland Nov. 7-9, 2008.
Harper, Kenneth, "Advances in Therapy for Venous Disease Ambulatory Phlebectomy Cleaning Up Branch Varicose veins," American College of Phlebology, Marcoisland Nov. 7-9, 2008.
Rush, Janet, "Neurological and Visual Symptoms Following Treatment of the Saphenous Veins with Two Formulations of Polidocanol Endovenous Microfoam," American College of Phlebology, Marcoisland Nov. 7-9, 2008.
Wakefield, T., "New Anticoagulants, (Total US 2002 VTE Events)" American College of Phlebology, Marcoisland Nov. 7-9, 2008.
Proebstle, Thomas, "One and Two Years Follow-Up of Radiofrequency Segmental Thermal Ablation (RSTA) of Great Saphenous Veins," American College of Phlebology, Marcoisland Nov. 7-9, 2008.
Wollmann, J.C., "Sclerosant Foams: Stabilities, Physical Properties and Rheological Behavior," *Phlebologie*, pp. 208-217 (Apr. 2010).
Hartke and Mutschler, "Sauerstoff (Oxygen)," DAB 9 Kommentar, vol. 3 pp. 3055-3059 (1986).
Diepenbrock, F.,"Phlebocide®" Gehes Codex, Berlin, p. 965 (1960).
Hohler, R. "*Characterization of the bubble size distribution in sclerosant foams*".
Kreussler Pharma,"Video K24 Transcript," (Jan. 28, 2003).
Kreussler Pharma, "Versushsauswertung" (Jan. 29, 2003).
Eckmann, D.M., "*Microvascular embolization following polidocanol microfoam sclerosant administration*," Dermatol. Surg. vol. 31 pp. 636-643 (Jun. 2005).
Forlee, M.V., "*Stroke after varicose vein foam injection therapy*," J. Vasc. Surg. vol. 43 pp. 162-164 (Jan. 2006).
Eckmann, D.M., "*Regarding 'Stroke after varicose vein foam injection therapy*,'" J. Vasc. Surg. vol. 44 p. 225 (Jul. 2006).
O'Hare, J.L. "The use of foam sclerotherapy for varicose veins: A survey of the members of the Vascular Society of Great Britain and Ireland," Eur. J. Vasc. Endovasc. Surg. vol. 34: 232-35 (2007).
Sebba, F., "Chapter 5: Colloidal gas aphrons," Foams & Biliquid Foams-Aphrons pp. 63-78 (1987).
Raven, J.P., "Dry micrfoams: formation and flow in a confined channel," Eur. Phys. J. B. vol. 51 pp. 137-143 (2006).
Belcaro, G., "*Foam-sclerotherapy, surgery, sclerotherapy, and combined treatment for varicose veinsL A 10-year, prospective, randomized, controlled trial (VEDICO\* Trial)*," Angiology vol. 54 pp. 307-315 (2003).
Hamel-Desnos, C. "Efficacy of sclerosing foams: summary of the main published clinical trials," Angeologie vol. 56 pp. 39-44. (2004).
Ganan-Calvo, A.M. "*Coarsening of monodisperse wet microfoams*," Applied Physics Letters vol. pp. 4989-4991 (Jun. 2004).
Breu, F.X., "*Reversible neurologische Komplikationen bei der Schaum-Sklerotherapie*," Phlebologie pp. 115-116 (2006).
Rush, J.E., "*Neurological and visual symptoms following treatment of the great saphenous vein with two formulations of polidocalnol endovenous microfoam*." Phlebology vol. 24 pp. 85-95 (2009).

Sylvoz, N. "*Polidocanol induced cardiotoxicity: a case report and review of the literature*," J. des Maladies Vasculaires vol. 33 pp. 234-238 (2008).
Guex, J., "*Immediate and midterm complications of sclerotherapy: report of a prospective multicenter registry of 12,173 sclerotherapy sessions*," Dermatol. Surg. vol. 31 123-28 (2005).
Simpson, P. "D1 Syringe," (Oct. 13, 2008).
Bruke, V.H., "*Die kombinierte schaumverodung der varizen*," Wiener Medizinische Wochenschrift pp. 111-113. (1954).
Office Action dated Dec. 15, 2009 for U.S. Appl. No. 10/522,529.
Notice of Abandonment dated Mar. 10, 2011 for U.S. Appl. No. 10/522,529.
Notice of Allowance dated May 26, 2011 for U.S. Appl. No. 11/128,265.
Notice of Allowance dated Feb. 7, 2011 for U.S. Appl. No. 11/128,265.
Office Action dated Jun. 23, 2009 for U.S. Appl. No. 11/128,265.
Office Action dated Dec. 14, 2009 for U.S. Appl. No. 10/522,525.
Notice of Abandonment dated Jun. 29, 2010 for U.S. Appl. No. 10/522,525.
Notice of Allowance dated Mar. 9, 2010 for U.S. Appl. No. 10/522,528.
Issue Notification dated Jul. 7, 2010 for U.S. Appl. No. 10/522,528.
Notice of Allowance dated Jan. 25, 2010 for U.S. Appl. No. 10/522,527.
Issue Notification dated May 19, 2010 for U.S. Appl. No. 10/522,527.
Co-pending U.S. Appl. No. 12/765,980, filed Apr. 23, 2010.
Office Action dated Aug. 5, 2010 for U.S. Appl. No. 11/914,190.
Notice of Abandonment dated Feb. 16, 2011 for U.S. Appl. No. 11/914,190.
Office Action dated Jun. 22, 2010 for U.S. Appl. No. 11/914,192.
Office Action dated Oct. 6, 2010 for U.S. Appl. No. 11/914,192.
Office Action dated Jul. 7, 2011, for U.S. Appl. No. 11/914,192.
Office Action dated Jan. 30, 2008 for U.S. Appl. No. 11/225,860, which issued as U.S. Patent No. 7,604,185 on Oct. 20, 2009.
Office Action dated Oct. 8, 2008 for U.S. Appl. No. 11/225,860, which issued as U.S. Patent No. 7,604,185 on Oct. 20, 2009.
U.S. Appl. No. 10/342,329, which abandoned on Sep. 26, 2008.
Office Action dated Dec. 13, 2004, for U.S. Appl. No. 10/342,329, which abandoned on Sep. 26, 2008.
Office Action dated Nov. 30, 2005, for U.S. Appl. No. 10/342,329, which abandoned on Sep. 26, 2008.
Office Action dated Jul. 31, 2006, for U.S. Appl. No. 10/342,329, which abandoned on Sep. 26, 2008.
Office Action dated Jan. 30, 2007, for U.S. Appl. No. 10/342,329, which abandoned on Sep. 26, 2008.
Office Action dated Feb. 4, 2008, for U.S. Appl. No. 10/342,329, which abandoned on Sep. 26, 2008.
U.S. Appl. No. 12/184,989.
Office Action dated Sep. 1, 2010, for U.S. Appl. No. 12/184,989.
Office Action dated May 11, 2011, for U.S. Appl. No. 12/184,989.
U.S. Appl. No. 09/979,655, which issued as U.S. Patent No. 6,942,165 on Sep. 13, 2005.
Office Action dated Apr. 29, 2004, for U.S. Appl. No. 09/979,655, which issued as U.S. Patent No. 6,942,165 on Sep. 13, 2005.
Office Action dated May 5, 2006, for U.S. Appl. No. 11/171,293, which issued as U.S. Patent No. 7,357,336 on Apr. 18, 2008.
Office Action dated Dec. 11, 2008, for U.S. Appl. No. 11/171,293, which issued as U.S. Patent No. 7,357,336 on Apr. 18, 2008.
U.S. Appl. No. 12/039,341, which abandoned on Aug. 17, 2009.
Office Action dated Dec. 19, 2008, for U.S. Appl. No. 12/039,341, which abandoned on Aug. 17, 2009.

\* cited by examiner

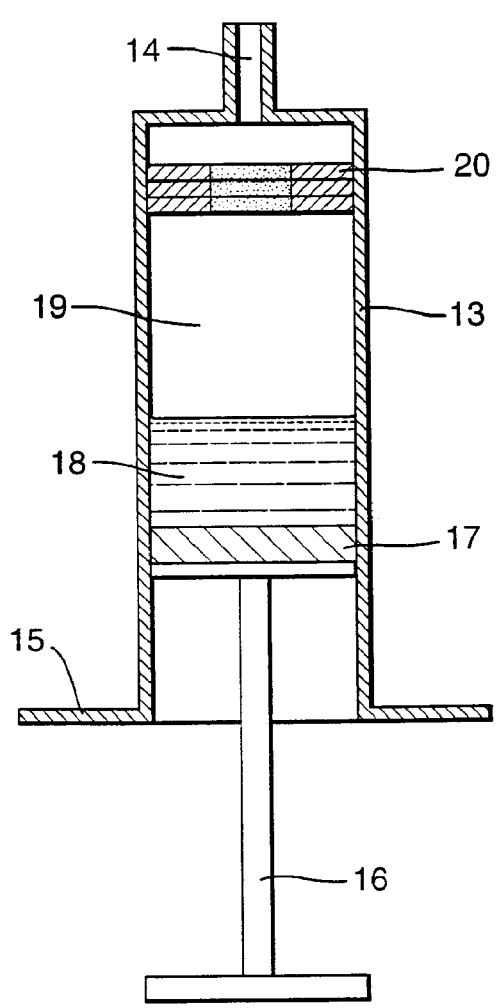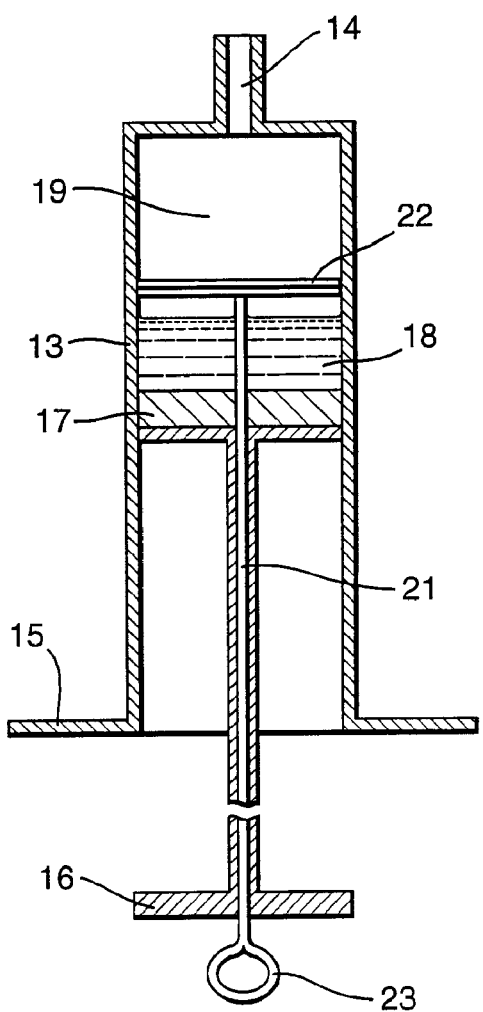

GENERATION OF THERAPEUTIC MICROFOAM

This is a Continuation of application Ser. No. 12/039,341, filed Feb. 28, 2008 now abandoned, which is a Divisional of application Ser. No. 11/171,293, filed Jul. 1, 2005, now U.S. Pat. No. 7,357,336, which is a Continuation of application Ser. No. 09/979,655, filed Apr. 12, 2002, now U.S. Pat. No. 6,942,165, which is the U.S. National Stage Application of International Application No. PCT/GB00/02045, filed May 26, 2000, which claims priority from United Kingdom Application No. 9912356.4, filed May 26, 1999. The disclosures of all applications cited in this paragraph are incorporated herein by reference.

The present invention relates to the generation of microfoam comprising a sclerosing material, particularly a sclerosing liquid, which is suitable for use in the treatment of various medical conditions involving blood vessels, particularly varicose veins and other disorders involving venous malformation.

Sclerosis of varicose veins is based on the injection into the veins of liquid sclerosant substances which, by inter alia causing a localised inflammatory reaction, favour the elimination of these abnormal veins. When a sclerosing substance is injected in liquid form, it is mixed with the blood contained in the vein and is diluted in an unknown proportion. The results are uncertain, owing to over- or under-dosage, and are limited to short varicose segments. As the size of the varicose veins to be injected decreases, this dilution is less and the results obtained are more predictable.

Until recently, sclerosis was a technique selected in cases of small and medium varicose veins, those with diameters equal to or greater than 7 mm being treated by surgery. Sclerosis and surgery complemented one another but sclerosis treatment continued not to be applicable to large varicose veins. In these large varicose veins, if a sclerosing substance was injected, its concentration in the vein, its homogeneous distribution in the blood, and the time for which it is in contact with the internal walls of the vessel treated were not known.

In 1946, Orbach injected a few cubic centimeters of air into small varicose veins and confirmed a displacement of the blood inside the vessel which was occupied by the injected air. A sclerosing solution introduced immediately afterwards was more effective than if it had been injected into the blood. However, in thick varicose veins, when air is injected the phenomenon described of the displacement of the blood by the injected air does not occur but the air forms a bubble inside the vein which makes the method ineffective in these vessels.

The same author had the idea, a few years later, of injecting foam obtained by agitation of a container containing sodium tetradecyl sulphate, which is an anionic sclerosing detergent with a good foaming capability. The method was of little use owing to the large size of the bubbles formed and was dangerous owing to the side effects of atmospheric nitrogen which is only slightly soluble in blood. Both methods had limited practical repercussion being used only in small varicose veins.

An injectable microfoam suitable for therapeutic uses has now been developed and is described in EP 0656203 and U.S. Pat. No. 5,676,962 (incorporated herein by reference). These patents describe a microfoam produced with a sclerosing substance which, when injected into a vein, displaces blood and ensures that the sclerosing agent contacts the endothelium of the vessel in a known concentration and for a controllable time, achieving sclerosis of the entire segment occupied.

The advantages of use of this foam are that it allows the concentration of the sclerosing agent in the blood vessel to be known, since the microfoam displaces the blood and is not diluted therein in to the same extent as a simple liquid would be. Furthermore it allows homogeneous distribution of the sclerosis product in the vein to be ensured and the time for which it is kept in contact with the internal walls of the vein to be controlled. None of which factors is known precisely or is controllable with the use of sclerosing agents in simple liquid form.

The preparation of such a microfoam may be carried out with a solution of any sclerosing substance, particularly polidocanol, alkali metal tetradecyl sulphate eg. sodium salt, hypertonic glucose or gluco-saline solutions, chromic glycerol, ethanolamine oleate, sodium morrhuato or iodic solutions.

However, this known method requires production of microfoam by the physician, pharmacist or an assistant immediately prior to administration to the patient. Such procedure allows for variation of agent depending upon the person preparing it, with content of gas, bubble size and stability all needing attention with respect to the condition being treated. It also requires a high degree of care and knowledge that may be difficult to replicate under pressure, ie. when time available to prepare the foam is short.

The method particularly described in the aforesaid patents uses a high speed beating action with a brush to generate a foam of correct property. Other reported techniques in use do not produce such uniform, stable or injectable microfoam and notably include those where gas is bubbled, eg sparged into the sclerosant, eg. by leakage into a sclerosant filled syringe from around the side of the syringe plunger.

Furthermore, a problem in using air as the gas for producing the foam is the perception that large volumes of nitrogen should not unnecessarily be introduced into patients, particularly where large vessels are being filled with foam and eliminated. Gas embolism with nitrogen remains a possibility.

The solubility of physiological gases in aqueous fluids, such as blood, varies considerably. Thus while nitrogen is almost twice as insoluble in water as oxygen at STP, carbon dioxide is over fifty times as soluble in aqueous liquids as nitrogen and over twenty five times as soluble as oxygen.

TABLE 1

| Solubility of Gases in water at STP | |
|---|---|
| Gas | Mole Fraction Solubility $10^{-5}$ |
| Helium | 0.7 |
| Nitrogen | 1.18 |
| Oxygen | 2.3 |
| Xenon | 7.9 |
| Nitrous oxide | 43.7 |
| Carbon dioxide | 61.5 |

At the present time it is perceived that production of such microfoam with gases incorporating high proportions of gas that is readily dispersed in blood, such as carbon dioxide, would be desirable for the purposes of minimising the prospect of the treatment producing a gas embolism. However, it is also perceived by practitioners that this is difficult task due to its high solubility in water.

It would also be desirable to provide a relatively stable microfoam of uniform character that is readily producible by use of a relatively simple and reliable mechanism, rather than one involving use of high speed mixing or beating, the time of performance of which may affect foam property.

It is particularly desirable that the microfoam so produced may be passed through a needle of gauge suitable for injecting into blood vessels without being significantly converted back to its separate gas and liquid components and/or changing characteristics such as significantly increasing bubble sizes.

Such a needle may be of very small diameter, eg a 30 gauge needle (0.14 mm interior diameter). More typically it will be larger eg. an 18 to 22 gauge needle (interior diameter 0.838 to 0.394 mm), more preferably 19 to 21 gauge (interior diameter. 0.686 mm).

The rate at which the foam is passed down the needle can be such that any foam might be broken down, but it is desirable that a foam is produced that does not break down under normal injection conditions, ie. at rates compatible with control of entry of foam into a vein. For example, it should withstand injection at rates of 0.1 to 0.5 ml/second, more preferably 0.3 to 1 ml/second for a 19 to 21 gauge needle.

It is still further desirable to provide a device that is of sterile type with regard to the foam it generates particularly with regard to micro-organisms and pyrogens.

It is particularly desirable to provide a sealed device that operates to produce foam of set property suitable for a given medical procedure without technical input from the physician who will perform the procedure, or assistants thereof.

One form of device that could potentially provide these desired properties would be an aerosol dispenser of a type that produces foams. However, for the purposes of generating a microfoam to be injected into a human or animal body, it is undesirable to have a propellant gas of the type usually employed in aerosol canisters, eg such as isopropane. This determines that the gas from which the foam is to be made must itself be pressurised to allow production of foam.

Water soluble gases such as carbon dioxide have been found by the inventors to be incapable of producing a stable foam when generated by merely being passed through a standard aerosol valve under pressure, such as might be expected to convert a detergent solution such as one of polidocanol or sodium tetradecylsulphate to a foam. They have determined that when this gas is used under pressure to propel a sclerosing agent solution through a conventional aerosol valve the foam produced, while initially containing at least some microfoam structure, is not sufficiently stable to be applied to the treatment of blood vessels as described in EP 0656203 and U.S. Pat. No. 5,676,962. Such foam is furthermore incapable of being passed through a syringe needle without significant reversion to liquid and gas phases. It will be realised by those skilled in the art that the microfoam technique exploits the ability of the gas to deliver the sclerosant solution to the wall of the vessel to be treated, rather than to allow its dilution in blood as in the liquid phase.

Aerosol units that are capable of producing foam have been described in the prior art. U.S. Pat. No. 3,471,064 describes a device wherein air is drawn into a foamable liquid through a series of small holes in the dip tube of the unit. Such a device is not sterile in operation as it relies on its contents being open to the air. Foam so produced would appear to vary in properties dependent upon how much air is drawn in. A further device is described in U.S. Pat. No. 3,428,222 and utilises a wicking and foaming element in a compressible container that again draws in air to produce foam.

U.S. Pat. No. 3,970,219 describes sealed aerosol devices which are capable of using pharmacologically inert gases to foam and expel liquid compositions, It describes devices which produce foam by passage of the propellant through a material having pores of 0.01 to 3 mm diameter from a lower propellant gas holding chamber to an upper foam holding chamber. The liquid to be foamed sits in the upper chamber or is absorbed onto the porous material by shaking the container or is wicked up from a lower chamber. This patent teaches that liquid from foam in the upper chamber drains down into the lower chamber, such that the thinnest walled bubbles are expelled, and teaches that the propellant gas should be 'less soluble', such as nitrogen, fluorocarbon or hydrocarbon, where aqueous liquids are to be foamed.

Similar bubbler devices are used in accessories for use with 'environmentally friendly' aerosol devices that operate using air under low pressure, ie. hand pump conditions. Two such devices are supplied by Airspray International as the 'Airspray® Finger Pump Foamer' and 'Airspray Mini-Foamer'. The former is said to be suitable for simple water based formulations while the latter is suggested for cosmetics, hair or skin care preparations. A second such device is provided as an optional extra in the Swedspray/Eurospray® hand pump device as a foaming nozzle. This device is marketed as being suitable for use to 'make you own cleansing foam or shaving lather'.

However, the present inventors have found that use of the available hand-pump devices themselves, which in any case are not sterile, cannot produce good microfoam with high loadings of carbon dioxide due to outgassing, nor with inclusion of significant amounts of glycerol which otherwise stabilises microfoam. Furthermore, when significant back-pressure is applied to the outlet of such device, such as when attached to a syringe to be loaded for injecting the foam, stuttering occurs. Use of low ejection velocity with this device can cause wetting at the nozzle which results in large bubbles caused by air entrapment. In any case the foams so produced, whether with oxygen or carbon dioxide, tend to be very dry, with resultant need for high concentration of sclerosant to be included, and tendency to break up on passage down a needle.

It is preferred not to unnecessarily use high concentrations of sclerosant in the solution as this could result in overdosage should a dispensing device fail and deliver a more dense microfoam, ie. including a higher proportion of liquid than intended.

Thus there is a need to provide a method and device that are capable of producing a uniform injectable microfoam made with a relatively low concentration of a sclerosing agent and a significant amount of a blood dispersible gas in sterile fashion without volatile liquid propellants or the need for the operator to directly be concerned in control of its parameters.

The present applicants have now provided a method and devices capable of addressing at least some of the aforesaid needs and have produced a novel stable injectable sclerosing microfoam with that method and devices.

For the purpose of this application terms have the following definitions: Physiologically acceptable blood dispersible gas is a gas that is capable of being substantially completely dissolved in or absorbed by blood. A sclerosant liquid is a liquid that is capable of sclerosing blood vessels when injected into the vessel lumen. Scleropathy or scelrotherapy relates to the treatment of blood vessels to eliminate them. An aerosol is a dispersion of liquid in gas. A major proportion of a gas is over 50% volume/volume. A minor proportion of a gas is under 50% volume/volume A minor amount of one liquid in another liquid is under 50% of the total volume. Atmospheric pressure and bar are 1000 mbar gauge. Half-life of a microfoam is the time taken for half the liquid in the microfoam to revert to unfoamed liquid phase.

In a first aspect of the present invention there is provided a method for producing a microfoam suitable for use in scleropathy of blood vessels, particularly veins, characterised in that it comprises passing a mixture of a physiologically acceptable blood dispersible gas and an aqueous sclerosant liquid through one or more passages having at least one cross-sectional dimension of from 0.1 to 30 µm, the ratio of gas to liquid being controlled such that a microfoam is produced having a density of between 0.07 g/ml to 0.19 g/ml and a half-life of at least 2 minutes.

Preferably the microfoam is such that 50% or more by number of its gas bubbles of 25 µm diameter and over are no more than 200 µm diameter.

Preferably the gas/liquid ratio in the mix is controlled such that the density of the microfoam is 0.09 g/ml to 0.16 g/ml, more preferably 0.11 g/ml to 0.14 g/ml.

Preferably the microfoam has a half-life of at least 2.5 minutes, more preferably at least 3 minutes. The half-life may be as high as 1 or 2 hours or more, but is preferably less than 60 minutes, more preferably less than 15 minutes and most preferably less than 10 minutes.

Half-life is conveniently measured by filling vessel with a known volume and weight of foam and allowing liquid from this to drain into a graduated vessel, the amount drained in a given time allowing calculation of half-life ie. of conversion of microfoam back into its component liquid and gas phases. This is preferably carried out at standard temperature and pressure, but in practice ambient clinic or laboratory conditions will suffice.

Advantageously and preferably the method provides a foam characterised in that at least 50% by number of its gas bubbles of 25 µm diameter and over are of no more than 150 µm diameter, more preferably at least 95% of these gas bubbles by number are of no more than 280 µm diameter. Still more preferably at least 50% by number of these gas bubbles are of no more than 130 µm diameter and still more preferably at least 95% of these gas bubbles by number are of no more than 250 µm diameter.

Preferably the mixture of gas and sclerosant liquid is in the form of an aerosol, a dispersion of bubbles in liquid or a macrofoam. By macrofoam is meant a foam that has gas bubbles that are measured in millimeters largest dimension, eg. approximately 1 mm and over, and over such as can be produced by lightly agitating the two phases by shaking. Preferably the gas and liquid are in provided in the form of an aerosol where a source of pressurised gas and a means for mixing the two is provided to the point of use. It may be preferred that a macrofoam is first produced where the liquid and gas are brought together only at the point of use.

The ratio of gas to liquid used in the mixture is important in order to control the structure of the microfoam produced such that its stability is optimised for the procedure and the circumstances in which it is being carried out. For optimum foams it is preferred to mix 1 gram sclerosant liquid with from approximately 6.25 to 14.3 volumes (STP), more preferably 7 to 12 volumes (STP), of gas.

Preferably the physiologically acceptable blood dispersible gas comprises a major proportion of carbon dioxide and/or oxygen. Conveniently it may comprise a minor proportion of nitrogen or other physiologically acceptable gas. While a proportion of nitrogen may be present, as in air, the present invention provides for use of carbon dioxide and/or oxygen without presence of nitrogen.

In one preferred form the gas used is a mixture of carbon dioxide and other physiological gases, particularly containing 3% or more carbon dioxide, more preferably from 10 to 90% carbon dioxide, most preferably 30 to 50% carbon dioxide. The other components of this gas are preferably oxygen with a minor proportion only of nitrogen being preferred. Most preferably the other component is oxygen.

A further preferred form of gas comprises 50% vol/vol or more oxygen, the remainder being carbon dioxide, or carbon dioxide, nitrogen and trace gases in the proportion found in atmospheric air. One preferred gas is 60 to 90% vol/vol oxygen and 40 to 10% vol/vol carbon dioxide, more preferably 70 to 80% vol/vol oxygen and 30 to 20% vol/vol carbon dioxide. More preferred is 99% or more oxygen.

It is found that passing a stream of the sclerosant liquid and the gas under pressure through one or more passages of 0.1 µm to 30 µm as described provides a stable blood dispersible gas based sclerosant injectable microfoam that was previously though to be only producible by supply of high amounts of energy using high speed brushes and blenders.

Preferably the sclerosing agent is a solution of polidocanol or sodium tetradecylsulphate in an aqueous carrier, eg water, particularly in a saline. More preferably the solution is from 0.5 to 5% v/v polidocanol, preferably in sterile water or a physiologically acceptable saline, eg. in 0.5 to 1.5% v/v saline. Concentration of sclerosant in the solution will be advantageously increased for certain abnormalities such as Klippel-Trenaunay syndrome.

Polidocanol is a mixture of monolaurylethers of macrogols of formula $C_{12}C_{25}(OCH_2CH_2)_nOH$ with an average value of n of 9. It will be realised that mixtures with other alkyl chains, oxyalkyl repeat units and/or average values of n might also be used, eg. 7 to 11, but that 9 is most conveniently obtainable, eg. from Kreussler, Germany, eg as Aethoxysklerol.

Most preferably the concentration of sclerosant in the aqueous liquid is a 1-3% vol/vol solution, preferably of polidocanol, in water or saline, more preferably about 2% vol/vol. The water or saline also, in some cases at least, preferably contain 2-4% vol/vol physiologically acceptable alcohol, eg ethanol. Preferred saline is buffered. Preferred buffered saline is phosphate buffered saline. The pH of the buffer is preferably adjusted to be physiological, eg from pH6.0 to pH8.0, more preferably about pH7.0.

The sclerosant may also contain additional components, such as stabilising agents, eg foam stabilising agents, eg such as glycerol. Further components may include alcohols such as ethanol.

The aerosol, dispersion or macrofoam is preferably produced by mixing the gas and liquid from respective flows under pressure. The mixing conveniently is carried out in a gas liquid interface element such as may be found in aerosol canisters. The interface device may however be very simple, such as a single chamber or passage of millimeter dimensions, ie. from 0.5 to 20 mm diameter, preferably 1 to 15 mm diameter, into which separate inlets allow entry of gas and liquid. Conveniently the interface is of design which is commonly found in aerosol canisters but which is selected to allow the correct ratio of gas to liquid to allow formation of a foam of the presently defined density. Suitable inserts are available from Precision Valves (Peterborough UK) under the name Ecosol and are selected to produce the ratio specified by the method above.

However, the mixing of gas and liquid may also be brought about within a dip-tube leading from the sclerosant solution located in the bottom of a pressurised container where holes in the dip-tube allow gas to enter into a liquid stream entering from the bottom of the tube. In this case the holes may be of similar diameter to the Ecosol holes. Such holes may be conveniently produced by laser drilling of the dip-tube.

The one or more passages through which the aerosol or macrofoam so produced are passed to produce the stable microfoam preferably have diameter of from 5 µm to 25 µm, more preferably from 10 µm to 20 µm where simple passages are provided, such as provided by openings in a mesh or screen, eg. of metal or plastics, placed perpendicular to the flow of gas/liquid mixture. The passage is conveniently of circular or eliptical cross section, but is not necessarily so limited. A number of such meshes or screens may be employed along the direction of flow.

Most preferably the passages are provided as multiple openings in one or more elements placed across the flow. Preferably the elements are from 2 to 30 mm diameter, more preferably 6 to 15 mm diameter, face on to the flow, with 5 to 65% open area, eg 2% to 20% open area for woven meshes and 20% to 70% open area for microporous membranes. Openings in a porous material, such as provided in a perforated body, preferably provide several hundreds or more of such passages, more preferably tens or hundred of thousands of such passages, eg. 10,000 to 500,000, presented to the gas liquid mixture as it flows. Such material may be a perforated sheet or membrane, a mesh, screen or sinter. Still more preferably a number of sets of porous material are provided arranged sequentially such that the gas and liquid pass through the passages of each set. This leads to production of a more uniform foam.

Where several elements are used in series these are preferably spaced 1 to 5 mm apart, more preferably 2 to 4 mm apart eg. 3 to 3.5 mm apart.

For some embodiments of the present invention it is found that the passage may take the form of a gap between fibres in a fibrous sheet placed across the path of the gas/liquid flow, and the dimension described in not necessarily the largest diameter, but is the width of the gap through which the gas/liquid aerosol or macrofoam must flow.

Alternatively the method provides for passing the mixture of gas and liquid through the same set of passages, eg as provided by one or more such porous bodies, a number of times, eg. from 2 to 2,000, more preferably 4 to 200 times, or as many times as conveniently results in a microfoam of the required density set out above. It will be realised that the more times the microfoam passes through the meshes, the more uniform it becomes.

The pressure of the gas used as it is passed through the passages will depend upon the nature of the mechanism used to produce the foam. Where the gas is contained in a pressurised chamber, such as in an aerosol canister, in contact with the liquid, suitable pressures are typically in the range 0.01 to 9 bar over atmosphere. For use of meshes, eg 1 to 8 meshes arranged in series, having apertures of 10-20 μm diameter, 0.1 to 5 atmospheres over bar will, inter alia, be suitable. For use of 3-5 meshes of 20 μm aperture it is found that 1.5-1.7 bar over atmospheric is sufficient to produce a good foam. For a 0.1 m pore size membrane, a pressure of 5 bar or more over atmospheric pressure is preferred.

In one preferred form of the invention the passages are in the form of a membrane, eg of polymer such as polytetrafluoroeythylene, wherein the membrane is formed of randomly connected fibres and has a rated effective pore size which may be many times smaller than its apparent pore size. A particularly suitable form of this is a biaxilally oriented PTFE film provided by Tetratec™ USA under the trademark Tetratex®, standard ratings being 0.1 to 10 μm porosity. Preferred pore sizes for the present method and devices are 3 to 7 μm. This material may be laminated with a porous backing material to give it strength and has the advantage that one pass through may be sufficient to produce a foam that meets the use requirements set out above with regard to stability. However, it will evident to those skilled in the art that use of more than one such membrane in series will give a still more uniform foam for given set of conditions.

It is believed that the combination of provision of a stream of solution and gas under pressure through an aerosol valve and then flow through the passages, eg. pores in a mesh, screen, membrane or sinter provides energy sufficient to produce a stable aqueous liquid soluble gas, eg carbon dioxide and/or oxygen, based sclerosant microfoam that was previously though to be only producible by supply of high amounts of energy using high speed brushes and blenders as described in the prior art.

Preferably the method of the invention provides a microfoam having at least 50% by number of its gas bubbles of 25 μm diameter or over being no more than 120 μm diameter. Preferably at least 95% of its gas bubbles of 25 μm diameter or over are of no more than 250 μm diameter. Diameter of such bubbles may be determined by the method set out in the Example 6 set out herein.

A most preferred method of the invention provides a housing in which is situated a pressurisable chamber. For sterile supply purposes this will at least partly filled with a sterile and pyrogen free solution of the sclerosing agent in a physiologically acceptable aqueous solvent but otherwise may be charged with such at the point of use. This convenient method provides a pathway by which the solution may pass from the pressurisable chamber to exterior of the housing through an outlet and more preferably a mechanism by which the pathway from the chamber to the exterior can be opened or closed such that, when the container is pressurised, fluid will be forced along the pathway and through one or more outlet orifices.

The method is particularly characterised in that the housing incorporates one or more of (a) a pressurised source of the physiologically acceptable gas that is readily dispersible in blood, and (b) an inlet for the admission of a source of said gas; the gas being contacted with the solution on activation of the mechanism.

The gas and solution are caused to pass along the pathway to the exterior of the housing through the one or more, preferably multiple, passages of defined dimension above, through which the solution and gas must pass to reach the exterior, whereby on contact with, eg flow through, the passages the solution and gas form a the microfoam.

Preferably the gas and liquid pass through a gas liquid interface mechanism, typically being a junction between a passage and one or more adjoining passages, and are converted to an aerosol, dispersion of bubbles or macrofoam before passing through the passages, but as explained they may be converted first to a macrofoam, eg. by shaking of the device, eg, by hand, or mechanical shaking device.

In a second aspect of the present invention there is provided a device for producing a microfoam suitable for use in sclerophathy of blood vessels, particularly veins, comprising a housing in which is situated a pressurisable chamber containing a solution of the sclerosing agent in a physiologically acceptable solvent referred to in the first aspect; a pathway with one or more outlet orifices by which the solution may pass from the pressurisable chamber to exterior of the device through said one or more outlet orifices and a mechanism by which the pathway from the chamber to the exterior can be opened or closed such that, when the container is pressurised and the pathway is open, fluid will be forced along the pathway and through the one or more outlet orifices said housing incorporating one or more of (a) a pressurised source of physiologically acceptable gas that is dispersible in blood and (b) an inlet for the admission of said gas; the gas being in contacted with the solution on activation of the mechanism such as to produce a gas solution mixture said pathway to the exterior of the housing including one or more elements defining one or more passages of cross sectional dimension, preferably diameter, 0.1 μm to 30 μm, through which the solution and gas mixture is passed to reach the exterior of the device, said passing of said mixture through the passages forming a microfoam of from 0.07 to 0.19 g/ml density and of half-life at least 2 minutes.

Preferably the microfoam has 50% or more by number of its gas bubbles of 25 μm diameter and over of no more than 200 μm diameter.

More preferably the microfoam is from 0.09 to 0.16 g/ml density and most preferably of 0.11 μg/ml to 0.14 g/ml.

Preferably the microfoam has a half-life of at least 2.5 minutes, more preferably at least 3 minutes.

Advantageously and preferably this device provides a microfoam characterised in that at least 50% by number of its gas bubbles of 25 μm diameter and over are of no more than 150 μm diameter or less, more preferably at least 95% by number of these gas bubbles are of diameter 280 μm or less. Still more preferably at least 50% by number of these gas bubbles are of no more than 120 μm diameter and still more preferably at least 95% of these gas bubbles are of no more than 250 μm diameter.

Preferably the apparatus includes a chamber, eg such as in a sealed canister, charged with the blood dispersible gas and the sclerosant liquid, eg. in a single chamber, the device pathway including a dip tube with an inlet opening under the level of the liquid in this chamber when the device is positioned upright. Preferably the dip-tube has an outlet opening at a gas liquid interface junction where the gas, which resides in the chamber above the liquid, has access to the pathway to the device outlet. The pathway is opened or closed by a valve element which is depressed or tilted to open up a pathway to the exterior of the device, whereby the liquid rises up the dip tube under gas pressure and is mixed in the interface junction with that gas to produce an aerosol, dispersion of bubbles in liquid or macrofoam.

Either inside the pressurisable chamber disposed in the pathway to the valve, or on the downstream side of the valve, is provided an element having the one or more passages described in the first aspect mounted such that the gas liquid mixture, ie. dispersion of bubbles in liquid, aerosol or macrofoam, passes through the passage or passages and is caused to foam. This element may conveniently be located in a cap on the canister in between the valve mounting and an outlet nozzle. Conveniently depression of the cap operates the valve. Alternatively the element is within the canister mounted above the gas liquid interface.

In an alternate embodiment of this device the gas liquid interface may comprise holes in the dip tube above the level of the liquid in the canister inner chamber.

The gas pressure employed will be dependent upon materials being used and their configuration, but conveniently will be 0.01 to 9 bar over atmospheric, more preferably 0.1-3 bar over atmospheric, and still more preferably 1.5-1.7 bar over atmospheric pressure.

A preferred device of this aspect of the invention is of the 'bag-on-valve' type. Such device includes a flexible gas and liquid tight container, forming a second inner chamber within the pressurisable chamber, which is sealed around the dip-tube and filled with the liquid. More preferably the dip-tube has a one-way valve located at a position between its end located in the sclerosant liquid and the gas liquid interface junction, which when the passage to the exterior is closed, remains closed such as to separate the liquid from the physiologically acceptable blood dispersible gas around it in the chamber. On opening the pathway to the exterior, the one way valve also opens and releases liquid up the dip-tube to the gas liquid interface where an aerosol is produced which is in turn then passed through the passages to be converted to microfoam. A suitable one-way valve is a duck-bill type valve, eg such as available from Vernay Labs Inc, Yellow Springs, Ohio, USA. Suitable bag-on-valve can constructions are available from Coster Aerosols, Stevenage, UK and comprise an aluminium foil/plastics laminate.

Conveniently the one way valve is located at the top of the dip-tube between that and the gas liquid interface junction, ie. an Ecosol device. This allows filling of the bag before application of the one way valve, followed by sterilisation of the contents, whether in the canister or otherwise.

Such a preferred device has several potential advantages. Where oxygen is the gas, this is kept separate from the liquid before use and thus reduces possibility of oxygen radicals reacting with organic components in the liquid, eg. during sterilisation processes such as irradiation. Where carbon dioxide is the gas, storage can lead to high volumes of gas dissolving in the liquid, which on release to the atmosphere or lower pressure, could out-gas and start to destroy the microfoam too quickly. Such separation also prevents the deposition of solidified sclerosing agent components in the dimension sensitive orifices of the device in an unused can in storage or transit, particularly should that be oriented other than upright.

It is preferred that the gas liquid interface is provided as a defined orifice size device such as the Ecosol device provided by Precision Valve Peterborough UK. For a device where the passages of defined dimension are outside of the pressurised chamber, ie. mounted on the valve stem, the ratio of area of the gas holes to the liquid holes should be of the order of 3 to 5, preferably about 4. Where the passages are inside the pressurised chamber this is preferably higher.

A third aspect of the invention provides a device for producing a microfoam suitable for use in sclerotherapy of blood vessels, particularly veins, comprising a housing in which is situated a pressurisable chamber, at least part filled or fillable with a solution of a sclerosing agent in a physiologically acceptable solvent and/or a physiologically acceptable blood dispersible gas; a pathway by which the contents of the chamber may be passed to exterior of the housing through one or more outlet orifices and a mechanism by which the chamber can be pressurised such that its contents pass to the exterior along the pathway and through one or more outlet orifices said pathway to the exterior of the housing or the chamber including one or more elements defining one or more passages of cross sectional dimension, preferably diameter, 0.1 μm to 30 μm through which the contents of the chamber may be passed, whereby on passing through the passages the solution and gas form a microfoam of from 0.07 to 0.19 g/ml density and having a half-life of at least 2 minutes.

Preferably the microfoam is such that 50% or more by number of its gas bubbles of 25 μm or more diameter are of no more than 200 μm diameter.

Preferably the microfoam is of density 0.09 to 0.16 g/ml and more preferably of 0.1 g/ml to 0.14 g/ml. The preferred limits on bubble size are also as for the first and second aspects.

Preferably the microfoam has a half-life of at least 2.5 minutes, more preferably at least 3 minutes The elements defining the passages in the pathway or chamber may be static or may be moveable by manipulation of the device from outside of its interior chamber.

Such device may be conveniently constructed in the form of a syringe device, comprising a syringe barrel and a functionally co-operating syringe plunger defining a chamber, the plunger being the means for pressurising the chamber, that chamber containing the gas and liquid in use, but which is particularly characterised by being formed with the passages of aforesaid dimension adjacent or at the needle affixing end of the syringe body, eg at a luer connection opening.

In use such a device is partially charged with the required sclerosant liquid and then charged with the physiologically acceptable gas, or vice versa, by withdrawing the syringe plunger while connecting the luer opening to a source of each in turn. Alternatively these may be mixed beforehand as a macrofoam, or even as a microfoam which by its nature will be breaking down. Where the gas and liquid are charged as separate phases the syringe contents may be agitated such as to produce a foam. The plunger is then pushed into the syringe body whereby this foam passes through the passages and is converted to a microfoam having the required stability for the procedure concerned. Where the gas and liquid are charged together as a foam, operation of the plunger will provide the microfoam.

In a preferred embodiment of this device two chambers are provided and are linked to each other through a passage, eg including the syringe body luer connector orifice, via the one or more passages of 0.1 μm-30 μm dimension. In this manner reciprocation of a plunger in one or both of the chambers results in the gas and liquid being passed through the passages of defined dimension a desired number of times to produce the desired foam.

In an alternative embodiment an element defining a number of the passages of said dimension is provided within the chamber such that it can be moved in either direction to pass chamber contents through its passages. Conveniently this element may be mounted on a support, such as a support plunger rod coaxial to the syringe plunger rod. The element may incorporate any of the porous passageway defining items referred to above, but conveniently includes meshes or a porous membrane mounted with major surfaces perpendicular to the syringe barrel/chamber longitudinal axis such that movement of the support rod in either direction longitudinally results in a sweeping action by the element such that chamber contents, gas and liquid, are passed through the passages together. It will be realised that once such a device is charged with a suitable ratio of gas and liquid, it may also be shaken to give a loose macrofoam as a first step.

Preferably the housing is a container defining a chamber in which is situated the solution and gas under pressure and the pathway is a conduit leading from the chamber in the interior of the container to a valve closing an opening in the container wall.

Preferred forms of the one or more elements defining the multiple passages for use in the device of the present invention are meshes, screens or sinters. Thus one or more meshes or perforated screens or sinters will be provided, with some preferred forms employing a series of such elements arranged in parallel with their major surfaces perpendicular to the path of solution/gas expulsion.

It is preferred that all elements of any of the devices according to the invention having a critical dimension are made of a material that does not change dimension when exposed to aqueous material. Thus elements with such function such as the air liquid interface and the element defining the passages of 0.1 μm-30 μm dimension preferably should not be of a water swellable material such as Nylon 66 where they are likely to be exposed to the solution for more than a few minutes. Where such exposure is likely these parts are more preferably being fashioned from a polyolefin such as polypropylene or polyethylene.

Preferably the canister or syringe device is sized such that it contains sufficient gas and solution to form up to 500 ml of microfoam, more preferably from 1 ml up to 200 ml and most preferably from 10 to 60 ml of microfoam. Particularly the amount of gas under pressure in such canisters should be sufficient to produce enough foam to treat, ie. fill, at least one varicosed human saphenous vein. Thus preferred canisters of the invention may be smaller than those currently used for supply of domestic used mousse type foams. The most preferred canister device is disposable after use, or cannot be reused once opened such as to avoid problems of maintaining sterility.

It may be preferred to incorporate a device which maintains gas pressure in the canister as foam is expelled. Suitable devices are such as described under trademarked devices PECAP and Atmosol. However, where a significant headspace or pressure of gas is provided this will not be necessary.

In order to ensure that the microfoam delivered from devices of the invention is not 'outside' specification, ie. falls within the desired density, bubble size and half life parameters set out above, the present invention provides a further, fourth, aspect which provides a device which is positioned to receive microfoam emitted from the device of the second and third aspects of the invention, which device allows venting of the first portion of microfoam to waste and passage of a second portion of microfoam to a delivery device, such as a syringe, in sterile fashion.

A device of the fourth aspect comprises an inlet conduit being adapted to engage the outlet of a microfoam producing device of the second or third aspect in a microfoam tight fashion, the conduit being connected to and leading through a multipath tap capable of being set to direct microfoam passing down the conduit to one or both of first and second contiguous outlet conduits or to close the inlet conduit, at least one of the first and second outlet conduits being adapted to receive the luer connector of a syringe. Preferably the device also comprises one or more elements for engaging the device of the second or third aspect other than by its outlet nozzle to hold it securely, eg upright in the case of a canister with a dip-tube.

Preferably the device of the fourth aspect comprises a three-way tap. More preferably the device of the fourth aspect comprises a base element, sufficiently stable to mount a microfoam producing device of the second or third aspects when engaged thereby. Preferably the microfoam producing device is engaged by resilient elements which locate it securely adjacent the three-way tap whereby the inlet conduit can be attached to the microfoam producing device outlet conduit.

Particularly preferred the device of the fourth aspect comprises a base element adapted mount the microfoam dispensing device and an activating element which operates to cause the pathway to be opened the to the inlet conduit. In this manner when the multi-way tap is shut, the dispensing device contents remain therein, but when the multi-way tap is opened to either of its outlet conduits it immediately causes release of foam generated by the device.

A further aspect of the present invention provides improved microfoams for use in the elimination of blood vessels and vascular malformations that are made available by the method and devices of the invention characterised in that they comprise a physiologically acceptable gas that is readily dispersible in blood together with an aqueous sclerosant liquid characterised in that the microfoam has a density of from 0.07 to 0.19 g/cm and is capable of being passed down a 21 gauge needle without reverting back to gas and liquid by more than 10%, based on liquid content reverting back to unfoamed liquid phase.

Preferably the microfoam, on passage through said needle, does not revert back to unfoamed liquid by more than 5% based on liquid content, still more preferably by no more than 2%.

Preferably the microfoam is capable of being passed down a needle while retaining at least 50% by number of its gas bubbles of at least 25 μm diameter at no more than 200 μm diameter. This is conveniently measured under ambient conditions, more preferably at STP.

Preferably at least 50% by number of said gas bubbles remain at no more than 150 μm diameter and at least 95% of these bubbles at no more than 280 μm diameter. Preferably the microfoam has a half-life as measured by drainage through a funnel of 2 cm neck diameter and drainage path 10 cm of at least 2 minutes, more preferably 2.5 minutes and most preferably 3 minutes. This may be carried out at ambient temperature or STP. Most conveniently the funnel is pre-equilibrated in a water bath to ensure a temperature of 25° C. before drying and application of foam. Placing of a microfoam filled syringe upside down, without its plunger, above the funnel leading into a graduated receptacle allows convenient measurement of this parameter.

Preferably the gas includes less than 40% v/v nitrogen. Preferably the density of the microfoam is from 0.09 to 0.16 g/ml, more preferably 0.1 g/ml to 0.14 g/ml.

Advantageously and preferably at least 50% by number of the gas bubbles of 25 μm diameter or more are of no more than 120 μm diameter and still more preferably at least 95% of these gas bubbles are of diameter 250 μm or less.

Preferably the foam density, which is a measure of liquid/gas ratio, is from 0.13 to 0.14 g/cm and the half-life is at least 2.5 minutes. The foam more preferably does not move outside of its parameters of bubble size set out above in such time.

Preferably the gas consists of at least 50% oxygen or carbon dioxide, more preferably 75% or more oxygen or carbon dioxide and most preferably at least 99% oxygen or carbon dioxide, eg substantially 100% oxygen or carbon dioxide. Preferably the oxygen or carbon dioxide is medical grade.

Preferably the sclerosant is aqueous polidocanol or sodium tetradecyl sulphate.

When the sclerosant is aqueous polidocanol the concentration of polidocanol is from 0.5 to 4% vol/vol in the liquid, preferably being 1 to 3% vol/vol polidocanol and most preferably being 2% vol/vol in the liquid.

Advantageously the sclerosant is made up in water, but more advantageously is made up in a saline solution, particularly 10 to 70 mM phosphate buffered saline, eg. 50 mM phosphate buffered saline, and preferably of pH6 to pH8.0 eg. about pH 7.0. Advantageously the aqueous solution contains a minor amount of an alcohol, preferably 96% ethanol, eg at between 2 and 6% vol/vol, more preferably at about 4% vol/vol of 96% ethanol.

Addition of glycerol to the aforesaid sclerosant imparts a longer half-life to the resultant foam. However, glycerol also produces a tendency for the meshes to block up when using a mesh device as described above, so should be used carefully where the device it is produced from may be used multiple times or the bag-on-valve concept is used.

The present invention will now be described further by way of illustration only by reference to the following Figures and Examples. Further embodiments falling within the scope of the invention will occur to those skilled in the art in the light of these.

FIGURES

FIG. 1: Shows a cross-sectional view of a canister device of the second aspect of the invention as further described in Example 2 below.

Figure 2:
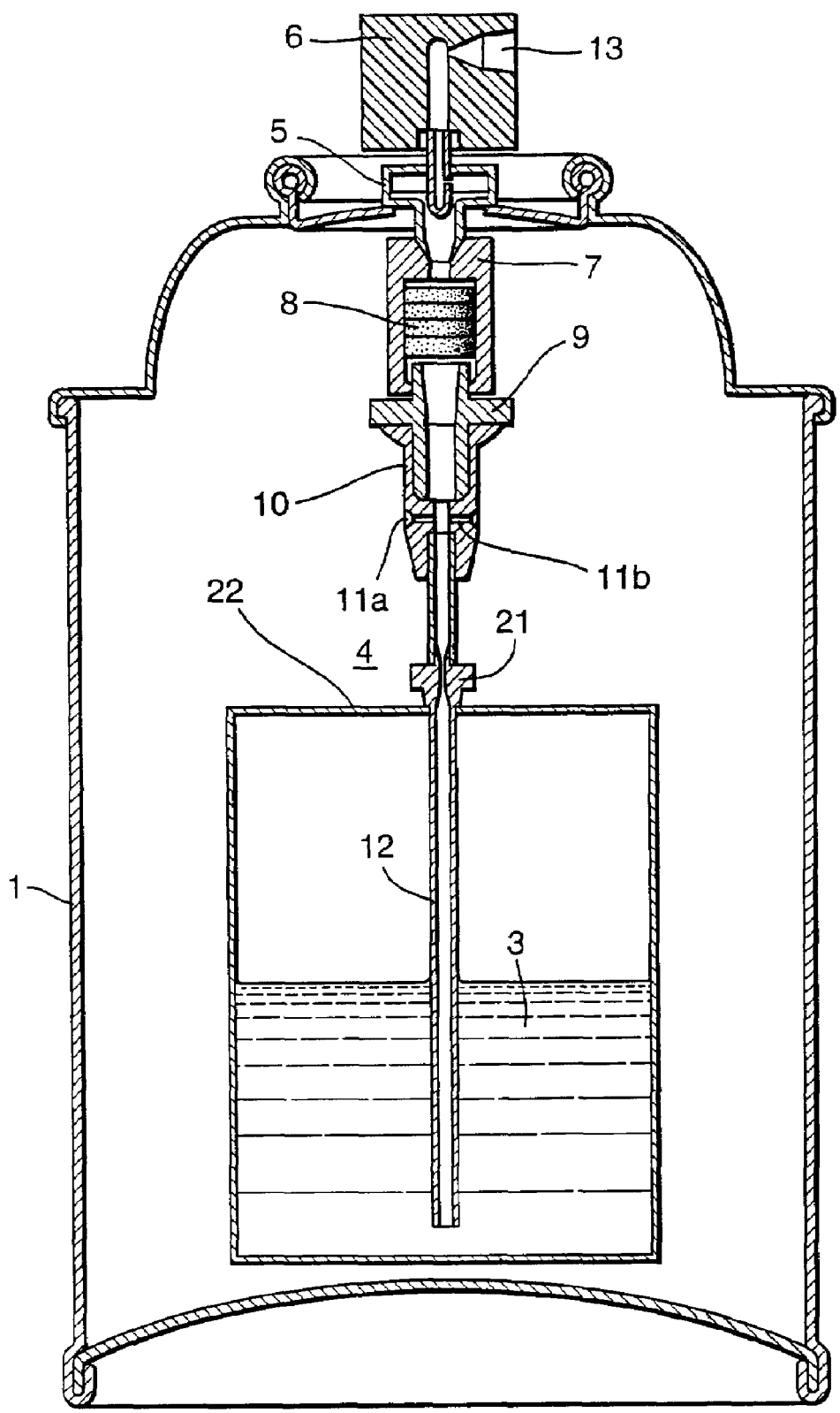

FIG. 2: Shows a cross-sectional view of a canister device of the second aspect incorporating a bag-on-valve reservoir for the sclerosant with the gas being in the outer chamber and separated therefrom by a one way duck-bill valve.

FIG. 3: Shows a cross-sectional view of a syringe-like device of the third aspect incorporating a set of meshes across its dispensing chamber.

FIG. 4: Shows a cross-sectional view of a syringe-like device of the third aspect incorporating a porous membrane supported on an inner plunger rod such that it can be reciprocated within the syringe chamber contents.

Figure 5:
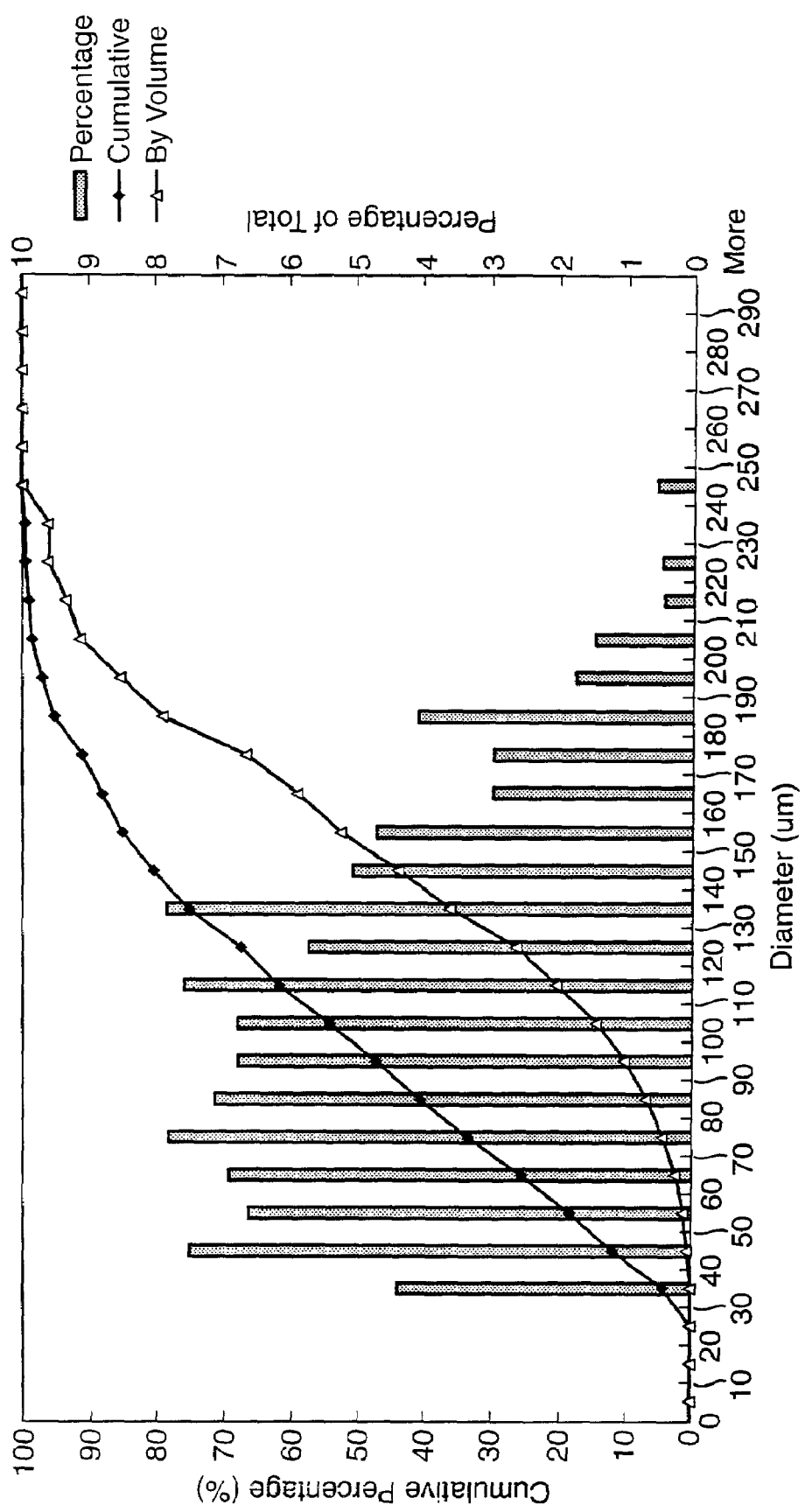

FIG. 5: Is a bar chart and graph illustrating distribution of gas bubble diameter in a preferred 0.13 g/ml oxygen/air/polidocanol microfoam of the fourth aspect.

Figure 6:
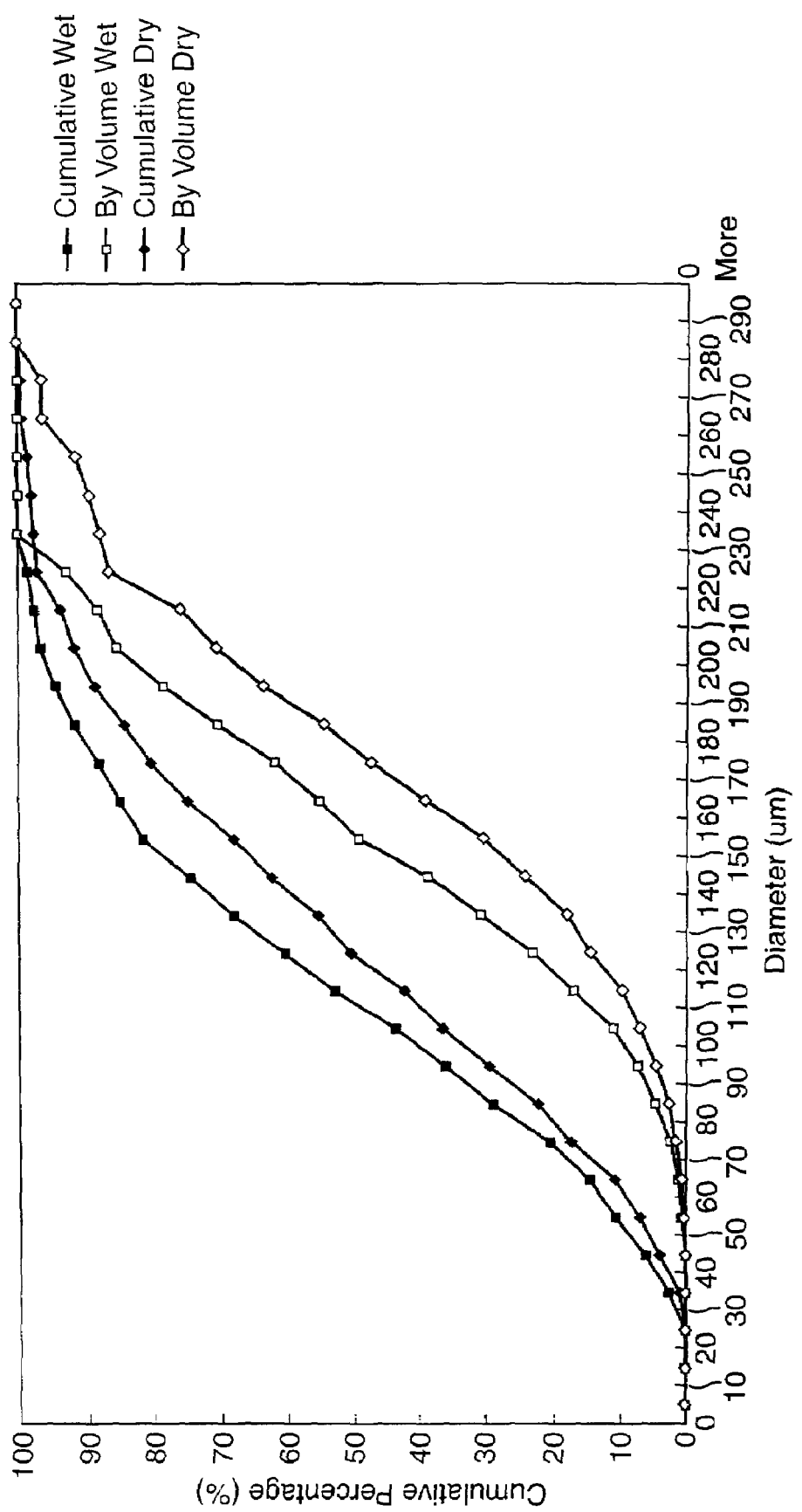

FIG. 6: Is a bar chart and graph illustrating distribution of gas bubble diameter in microfoams of 0.09 g/ml and 0.16 g/ml of the fourth aspect.

Figure 7:
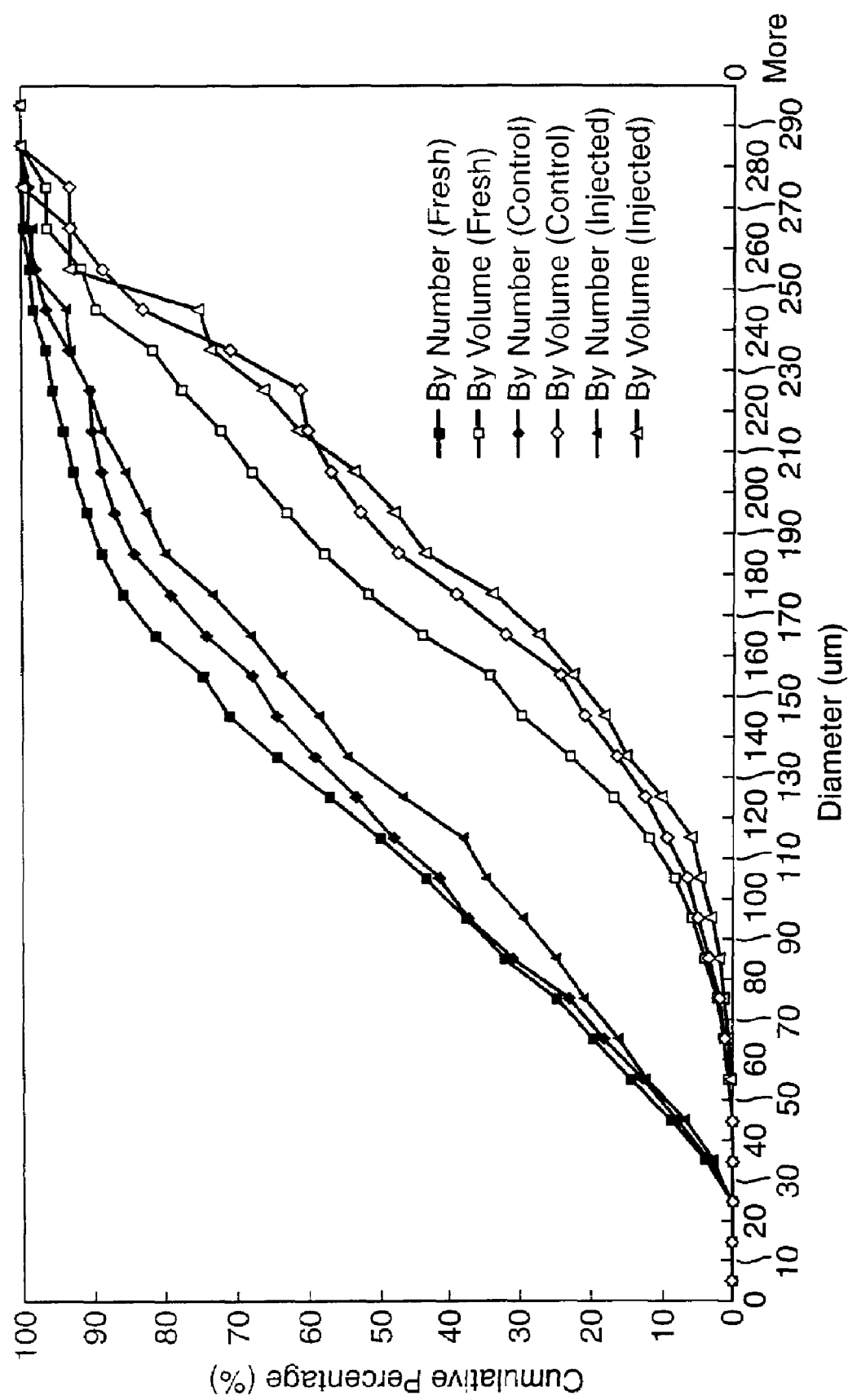

FIG. 7: Is a graph showing the effect of passing a preferred foam of the fourth aspect down a 21 gauge needle as compared to control fresh and similarly aged microfoams.

Figure 8:
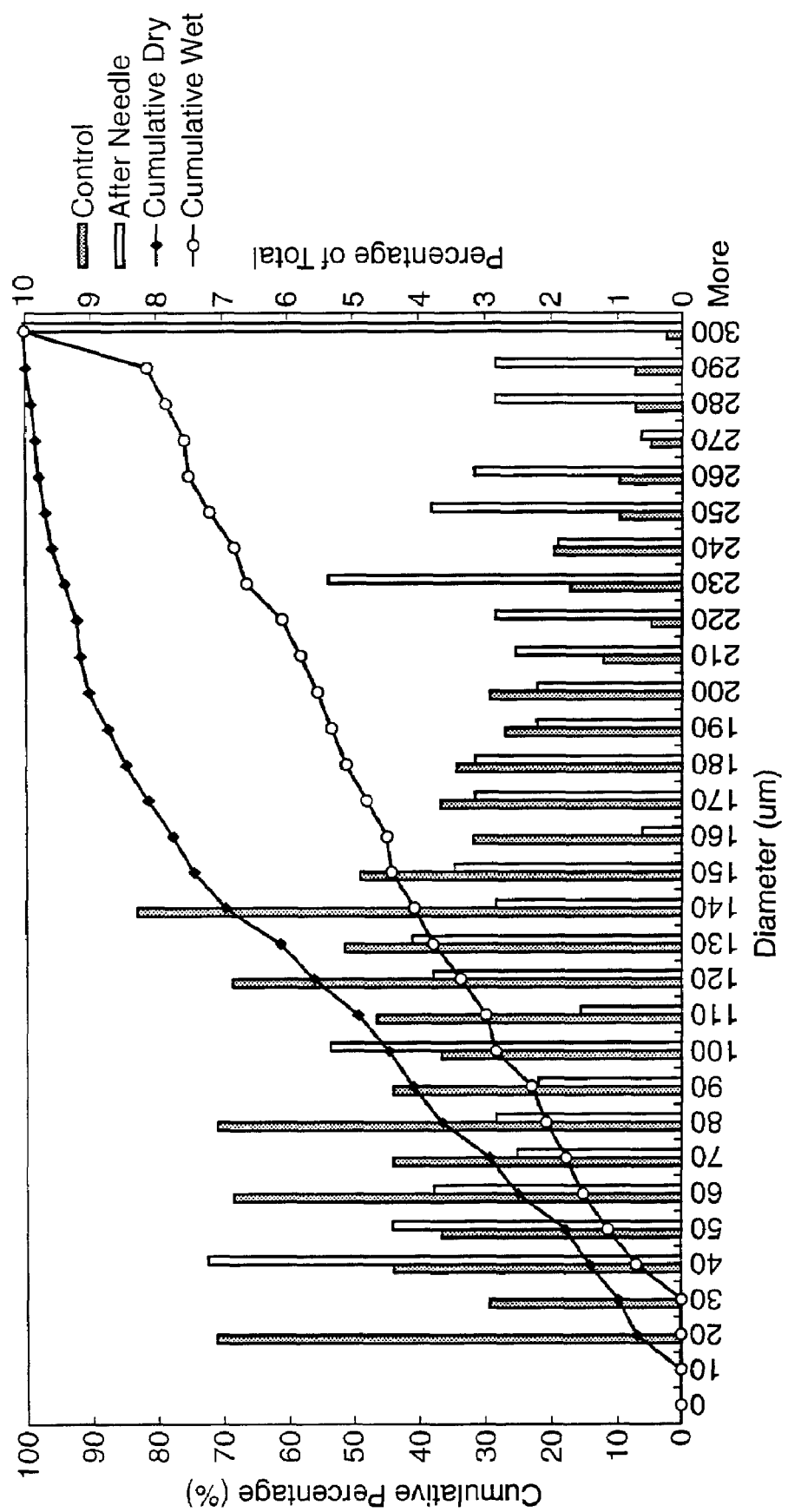

FIG. 8: Is a graph showing the effect of passing a 2% vol polidocanol solution dry microfoam of 0.045 g/ml, such as producible by use of a prior art bubbler device (Swedspray valve, Ecosol insert and head), down a 21 gauge needle.

Figure 9:
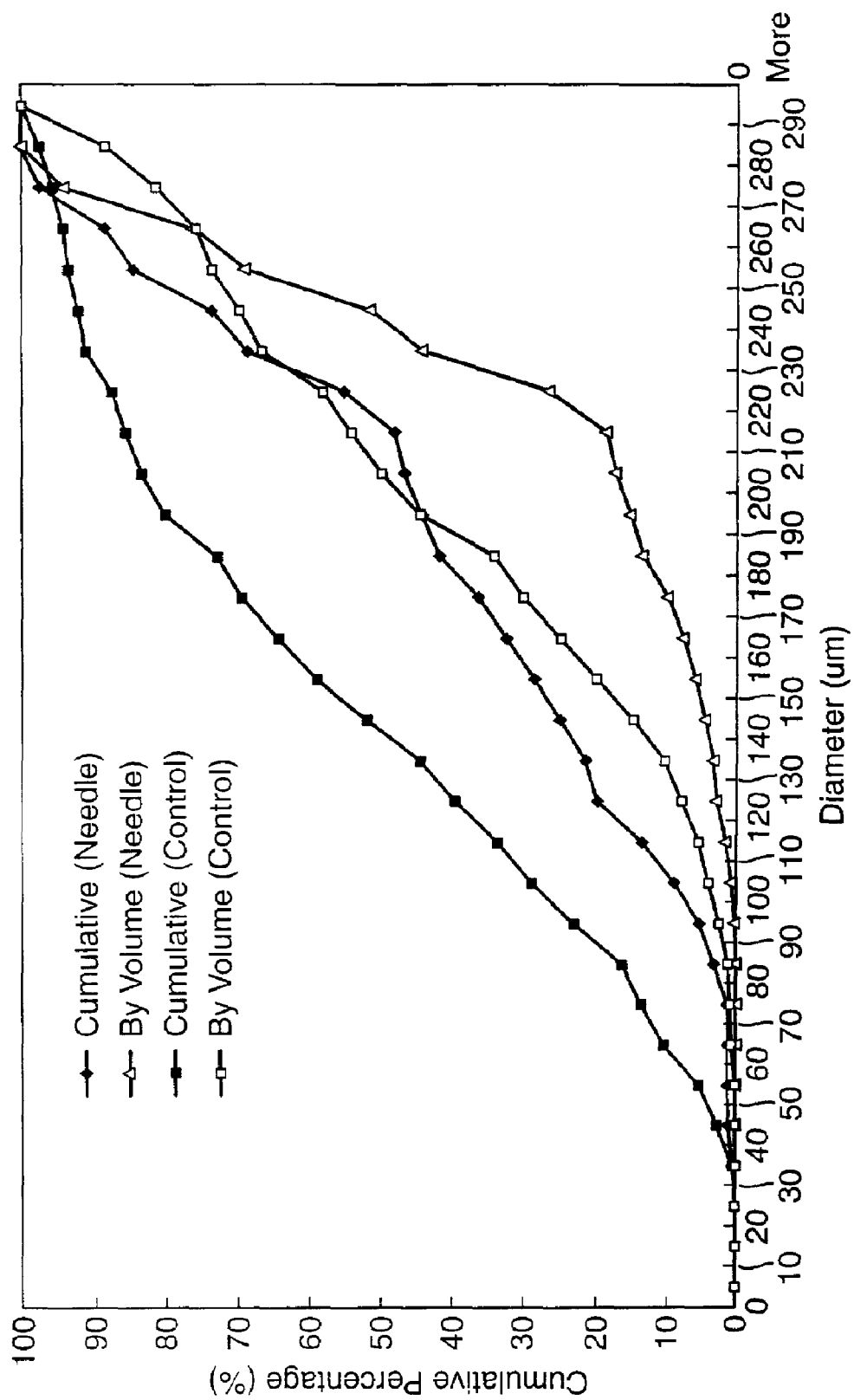

FIG. 9: Is a graph showing the effect of passing a 1% vol polidocanol dry microfoam of 0.045 g/ml such as producible by use of the prior art bubbler device (Swedspray valve, Ecosol insert and head), down a 21 gauge needle.

Figure 10:
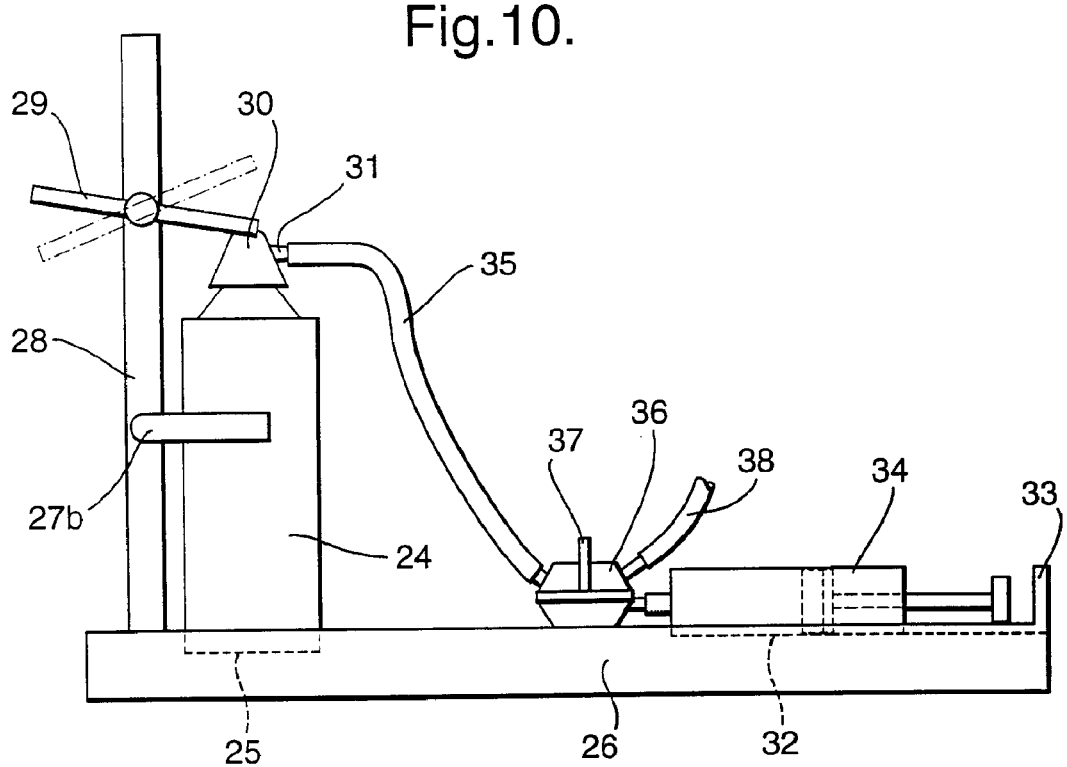

FIG. 10: is an elevation view of a syringe filling device of the fourth aspect.

Figure 11:
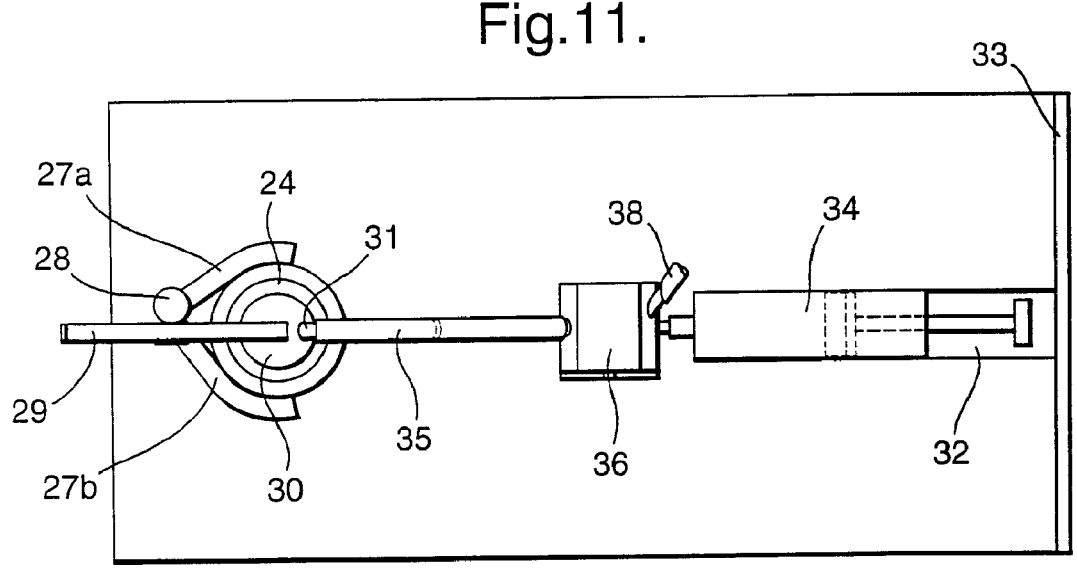

FIG. 11: Is a plan view of the device of FIG. 10.

EXAMPLES

Example 1

A standard aerosol canister with a one way depressible action valve is charged half full with a 3% v/v solution of polidocanol in sterile water and pressurised to 3 atmospheres with a 50:50 mix of carbon dioxide and oxygen. On the valve stem is mounted an actuator and delivery head which carries four plastics screens, just under 0.5 mm thick, perforated with 20 μm diameter passages, these screens being of the general type provided in the Swedspray-Eurospray foaming actuator cap ApRisC® device. The valve is fed through an Ecosol gas liquid interface insert from a dip-tube and the surrounding chamber. Gas inlet sizes (×2) into the insert are 0.006"×0.01" while the single liquid inlet is 0.024", as controlled by selecting Ecosol insert size. On depression of the head the aerosol valve releases pre-mixed solution and gas onto the screens whereupon a microfoam suitable for scleropathy and that is dimensionally stable for at least 2 minutes, preferably 5 minutes using glycerol in the is produced.

Example 2

FIG. 1 illustrates a further canister design of the invention wherein the passages through which the gas liquid mixture must travel are placed within the pressurised chamber, thus increasing hygiene of the device.

The canister is of standard 500 ml design with an aluminium wall (1), the inside surface of which is coated with an epoxy resin resistant to action of polidocanol and oxygen (eg Hoba 7940-Holden UK)). The bottom of the canister (2) is domed inward. The canister inner chamber (4) is pre-purged with 100% oxygen for 1 minute, containing 15 ml of a 2% vol/vol polidocanol/20 mmol phosphate buffered saline solution (3) then filled with the oxygen at 2.7 bar gauge (1.7 bar over atmospheric). This is provided by overpressuring the polidocanol part filled can with 1.7 bar oxygen.

The dome provides a perimeter area around the bottom of the inner chamber in which a level of polidocanol solution is retained sufficient for the bottom open end of a dip tube to be submerged therein when the top of the dome is no longer covered with the solution. In this manner, by use of an indicia on the outside of the canister to indicate the position of the dip tube, the canister can be oriented to extract the last fraction of solution if desired. In practice a vertical orientation is sufficient.

A standard 1" diameter aerosol valve (5) (Precision Valves, Peterborough) is crimped into the top of the canister after sterile part filling with the solution and is activatable by depressing an actuator cap (6) to release content via an outlet nozzle (13) sized to engage a luer fitting of a syringe or multi-way connector (not shown). A further connector (7) locates on the bottom of the standard valve and mounts, preferably by interference fit, four Nylon 66 meshes held in high density polyethylene (HDPE) rings (8) all within an open ended polypropylene casing. These meshes have diameter of 8 mm and have a 15% open area made up of 20 μm pores, with the meshes spaced 3.5 mm apart by the HDPE rings.

A further connector (9) locates on the bottom of the connector holding the meshes and receives a housing (10) which mounts the dip tube (12) and includes gas receiving holes (11a, 11b) which admit gas from chamber (4) into the flow of liquid which rises up the diptube on operation of the actuator (6). These are conveniently defined by an Ecosol device with insert as before. Holes (11a, 11b) have cross-sectional area such that the sum total ratio of this to the cross-sectional area of the diptube is controlled to provide the required gas/liquid ratio. This is for example 0.010"×0.013" each hole (11a, 11b) to 0.040" liquid receiving hole.

Example 3

A further canister embodiment of the present invention is shown in FIG. 2, which is broadly as shown in FIG. 1, but for the inclusion of a modified 'bag-on-valve' arrangement. In this embodiment the polidocanol sclerosing solution (3) is enclosed in a foil bag (22), comprising an aluminium foil/plastics laminate (Coster Aerosols Stevenage UK) sealed in gas tight fashion to dip-tube (12). At the top end of the dip-tube is a one-way duck-bill valve (Vernay Labs Inc Ohio USA) that serves to prevent contact of polidocanol with the contents of the dip-tube (12) and chamber (4) until the valve (5) is operated. On said operation the valve (21) opens and polidocanol solution (3) is caused to rise up the dip-tube (12), whereby it becomes mixed with the air/oxygen gas mixture entering through holes (11a, 11b). In this manner the can may be safely sterilised with ionising radiations which may otherwise cause interactions between radical species in the gas and the organic component of the polidocanol solution. Such arrangement can also improve the operation of the canister with regard to start up of foam delivery. The bag (22) preferably substantially only contains the liquid (3), with no headspace gas above it.

Example 4

The device of this example is identical with that of Example 3, save that the polidocanol in the liquid is replaced with a sodium tetradecylsulphate at 1% vol/vol, all other ingredients being the same.

Example 5

FIG. 3 shows a syringe device that is specifically designed to produce microfoam according to the invention using the method of the invention. Syringe body (13) has a luer opening (14) and locating flanges (15) and cooperates with a plunger (16) to define a chamber (19). Chamber (19) is prefilled, or filled in use, with sclerosing solution (18), in this case polidocanol as above. The plunger has a sealing face (17) that is inert with respect to the polidocanol solution and which ensures that said solution does not escape around the sides of the plunger when that is depressed to pressurise the contents of chamber (19).

Located between the plunger sealing face (17) and luer opening (14) is a series of three spaced meshes (20) of the type and configuration referred to in Example 2. In this example the meshes are located such as to leave a space between them and the luer opening such that a physician can see the foam produced by passage of gas/liquid mixture through the meshes.

In operation such a syringe is preferably provided with the plunger pushed in such as to define a reduced chamber (19) volume filled with sclerosing solution with the luer opening sealed in a sterile fashion, eg. by a foil seal cap attached to its exterior. The cap is peeled off, the luer attached to a source of required blood dispersible gas and the plunger withdrawn to admit a required amount of gas to give a ratio of gas to liquid suitable such that when agitated, eg. by shaking the syringe, a macrofoam is produced containing a 7:1 to 12:1 ratio gas to liquid. For production of foam the plunger is depressed with an even pressure, such as to depress at 1 ml/second, and the macrofoam is converted to microfoam.

It will be realised that the microfoam could be directly applied to a patient, but more conveniently would be transferred directly to a chamber, eg a second syringe, where viewing of a large volume of foam such as would be required to eliminate a large saphenous vein, would be more readily performed. In this manner, should it be desired, the microfoam could be passed between the two chambers via the meshes in order to render it still more uniform in nature.

Example 6

FIG. 4 shows a further syringe device embodiment of the invention designed to produce microfoam according to the invention using the method of the invention. Syringe body (13) has a luer opening (14) and locating flanges (15) and cooperates with a plunger (16) to define a chamber (19). Chamber (19) is prefilled, or filled in use, with sclerosing solution (18), in this case polidocanol as above. The plunger has a sealing face (17) that is inert with respect to the polidocanol solution and which ensures that said solution does not escape around the sides of the plunger when that is depressed to pressurise the contents of chamber (19).

Passing down the central longitudinal axis of the plunger is a rod (21) mounting a porous Tetratex membrane (22) of effective pore size about 5 μm in a double ring mounting. The rod (21) has a handle (23) located outside the syringe chamber which allows the membrane to be moved independently of the plunger such as to force the contents of chamber (19) to pass through its pores.

In operation such a syringe is preferably provided with the plunger pushed in such as to define a reduced chamber (19) volume filled with sclerosing solution with the luer opening sealed in a sterile fashion, eg. by a foil seal cap attached to its exterior. The cap is peeled off, the luer attached to a source of required blood dispersible gas and the plunger withdrawn to admit a required amount of gas to give a ratio of gas to liquid. Eg. a 7:1 to 12:1 ratio gas to liquid. For production of foam the handle (23) on rod (21) is operated to pass the membrane up and down the chamber a number of times, eg 2 to 10 times, causing the gas and liquid to mix and produce foam. For dispensing of foam directly to a patient, or to another syringe or container, the rod (21) is withdrawn such that membrane mounting (22) abuts the plunger sealing face and the plunger is such depressed with an even pressure, eg. at 1 ml/second. Obviously when the foam is passed directly into a patient a suitable needle is affixed to the luer connection.

Example 6

A microfoam of the invention is produced in a device as described in Example 1, having critical passage and gas mixing dimensions as set out in Example 2 but differing therefrom in that mesh is located in the dispensing cap, downstream of the valve, while gas/liquid mixing occurs in an Precision Valves Ecosol insert device upstream of the valve. The chamber (500 ml) is charged with 15 ml of an aqueous solution containing per 100 ml polidocanol (Kreussler-Germany) (2 ml), 96% ethanol (4 ml) and 55 mmol Phosphate Buffer (pH7.0) (94 ml) with gas being air overpressured with 1.5 bar 100% oxygen. The characteristics of the microfoam produced on operation of the valve are shown in FIGS. 5 and 6. FIG. 5 shows bubble size distribution immediately after microfoam generation; foam density being 0.138 g/ml. FIG. 6 shows bubble size produced with varying ratio of gas to liquid, provided by altering the gas/liquid interface hole size (11a, 11b) to give foams of 0.09 g/ml (closed diamonds) and 0.16 g/ml (open circles). FIG. 7 shows the effect on bubble size distribution of a preferred microfoam (0.13 g/ml) after passage through a 21G needle: Open circles show fresh foam, crosses control foam aged to match injection time and closed diamonds show after passage through the needle. FIG. 8 shows the effect of passing a microfoam made using a Swedspray device density 0.045 g/ml through the needle. Closed diamonds are control aged while open circles are after needle passage.

Note, when 5% glycerol is added to the formulation, half life was increased to approximately 4 minutes.

Bubble sizes are calculated by taking up foam into a syringe through its luer opening, optionally attaching a 21G needle, and injecting foam between two glass slides that are separated using 23.25 micron diameter beads (eg. available as microspheres from Park Labs USA). Maxtascan/Global Lab Image technique was used to analyse bubble size. Diameters of uncompressed bubbles (Dr) were calculated from diameters of bubbles between slides (Df) using the equation $Dr=3\sqrt{3}Df^2x/2$ where x is the distance between the slides. These measurements thus are made at ambient temperature and pressure.

It will be realised that bubbles much smaller than 25 μm diameter may be present but not counted. The % figures given with respect to bubble thus relate to bubbles in the range 25 μm and above.

Example 7

For filling of a syringe with microfoam of the invention the bottom of a canister of Example 1, 2 or 3 is placed into a receiving recess in the base of a syringe filling device as shown in elevation in FIG. 10 and plan (FIG. 11). Canister (24) is inserted into a 1 cm deep recess (25) in a plastics base element (26), the recess being approximately 1 mm in diameter more than the canister such that a snug fit is provided. The canister is further supported by two resilient fixed arms (27a, 27b), fixed on vertical support rod (28) that deform to receive the canister diameter.

Just above the top of the position of the canister cap in use, the support rod (28) mounts an actuator arm that is lockable between a first actuating position (full lines) an and an off position (dotted lines). In the actuating position the arm depresses the canister actuator cap (30), thus opening the canister valve and causing microfoam to be released.

Also on the base (26) is a recess (32) sized to snugly receive a syringe (34) with its plunger. A stop element (33) is provided that is positioned such that on filling the plunger is limited in its range of longitudinal movement such that the syringe cannot be overfilled.

A flexible transparent plastics tube (35), inert to the sclerosant foam, is attached to the canister outlet nozzle (31) in use and is fixed to a three way valve (36) affixed to the base (26). The valve is operated by turning a tap (37) to one of three positions: (a) valve shut-no microfoam passage (b) valve open to waste (38) whereby any microfoam that by visual inspection of the contents of tube (35) appears unsuitable, is vented and (c) valve open to syringe, whereby a set amount of microfoam passes through the syringe luer and fills it until the syringe plunger abuts the stop (33)

Example 8

20 mls microfoam of Example 6 is loaded into a 20 ml syringe using the device of Example 7 and the syringe disengaged from the device. A 19 gauge needle is attached either directly to the syringe luer fitting or via a catheter. The microfoam is administered into to a varicose vein while its advance and final position is monitored using a hand held ultrasound scanner such that the fresh foam is restricted in location to the vein being treated. After between 1 and 5 minutes the vein contracts and subsequently becomes fibrosed.

The invention claimed is:

1. A method for producing a microfoam suitable for use in sclerotherapy of blood vessels characterized in that it comprises passing a mixture of a physiologically acceptable blood dispersible gas,
    wherein said gas comprises at least 50% vol/vol carbon dioxide, and an aqueous sclerosant liquid through one or more passages, the ratio of gas to liquid being controlled such that a microfoam is produced having a density of between 0.07 g/ml to 0.19 g/ml and has a half-life of at least 2 minutes.

2. A method as claimed in claim 1 the gas/liquid ratio in the mixture is controlled such that the density of the microfoam is 0.09 g/mL to 0.16 g/mL.

3. A method as claimed in claim 1 characterized in that at least 50% by number of the gas bubbles of 25 μm diameter and above are of no more than 200 μm diameter and at least 95% of these gas bubbles are no more than 280 μm diameter.

4. A method as claimed in claim 1 characterized in that at least 50% by number of the gas bubbles of 25 μm diameter and above are of no more than 150 μm diameter and at least 95% of these gas bubbles are no more than 250 μm diameter.

5. A method as claimed in claim 1 characterized in that the mixture of gas and sclerosant liquid is in the form of an aerosol, dispersion of bubbles in liquid or macrofoam.

6. A method as claimed in claim 1 characterized in that the ratio of gas to liquid used in the mixture is 1 gram sclerosant liquid to from 6.25 to 14.3 volumes of gas at standard temperature and pressure.

7. A method as claimed in claim 1 characterized in that the physiologically acceptable blood dispersible gas comprises a major proportion of carbon dioxide and/or oxygen.

8. A method as claimed in claim 1 characterized in that the aqueous sclerosant liquid is a solution of polidocanol or sodium tetradecylsulfate (STS) in an aqueous carrier.

9. A method as claimed in claim 8 characterized in that the carrier comprises a saline solution.

10. A method as claimed in claim 1 characterized in that the mixture of gas and liquid is passed through the same passage or passages a number of times.

11. A method as claimed in claim 1 characterized in that the gas is pressurized at 0.1 to 9 bar over atmospheric pressure.

12. A method as claimed in claim 11 characterized in that the gas is pressurized at 0.1 to 3 bar over atmospheric pressure.

* * * * *